(12) United States Patent
Akah et al.

(10) Patent No.: US 12,325,834 B2
(45) Date of Patent: *Jun. 10, 2025

(54) METHODS FOR PROCESSING A HYDROCARBON OIL FEED STREAM UTILIZING A DELAYED COKER AND STEAM ENHANCED CATALYTIC CRACKER

(71) Applicant: Saudi Arabian Oil Company, Dhahran (SA)

(72) Inventors: Aaron Chi Akah, Dhahran (SA); Qi Xu, Dhahran (SA); Musaed Salem Al-Ghrami, Dammam (SA); Zhonglin Zhang, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 291 days.

This patent is subject to a terminal disclaimer.

(21) Appl. No.: 17/865,804

(22) Filed: Jul. 15, 2022

(65) Prior Publication Data

US 2024/0018430 A1 Jan. 18, 2024

(51) Int. Cl.
*C10G 69/00* (2006.01)
*C01B 3/24* (2006.01)
(Continued)

(52) U.S. Cl.
CPC .............. *C10G 69/14* (2013.01); *C01B 3/24* (2013.01); *C07C 5/42* (2013.01); *C07C 11/06* (2013.01);
(Continued)

(58) Field of Classification Search
CPC .......... C10G 9/36; C10G 55/02; C10G 69/02; C10G 51/06; C10G 11/20; C10G 69/06;
(Continued)

(56) References Cited

U.S. PATENT DOCUMENTS

| 2,416,023 A | 2/1947 | Schulze et al. |
| 3,361,535 A | 1/1968 | Pollitzer et al. |

(Continued)

FOREIGN PATENT DOCUMENTS

| EP | 3578623 A1 | 12/2019 |
| WO | 2015128040 A1 | 9/2015 |

OTHER PUBLICATIONS

Notification of Transmittal of the International Search Report and the Written Opinion of the International Searching Authority, or the Declaration dated Oct. 6, 2023 pertaining to International application No. PCT/US2023/069860 filed Jul. 10, 2023, pp. 1-17.

(Continued)

*Primary Examiner* — Prem C Singh
*Assistant Examiner* — Brandi M Doyle
(74) *Attorney, Agent, or Firm* — DINSMORE & SHOHL LLP

(57) ABSTRACT

An integrated process for upgrading a hydrocarbon oil feed stream includes solvent deasphalting the hydrocarbon oil stream to form at least a deasphalted oil stream and heavy residual hydrocarbons, delayed coking the heavy residual hydrocarbons to form petroleum coke and a delayed coker product stream; hydrotreating the delayed coker product stream and the deasphalted oil stream to form a $C_3$-$C_4$ hydrocarbon stream, a light $C_{5+}$ hydrocarbon stream, and a heavy $C_{5+}$ hydrocarbon stream; dehydrogenating the $C_3$-$C_4$ hydrocarbon stream to form propylene and butylene; steam enhanced catalytically cracking the light $C_{5+}$ hydrocarbon stream to form a light steam enhanced catalytically cracked product stream including olefins, benzene, toluene, xylene, naphtha, or combinations thereof; and steam enhanced catalytically cracking the heavy $C_{5+}$ hydrocarbon stream to form a heavy steam enhanced catalytically cracked product (Continued)

including olefins, benzene, toluene, xylene, naphtha, or combinations thereof.

13 Claims, 4 Drawing Sheets

(51) Int. Cl.
- *C07C 5/42* (2006.01)
- *C07C 11/06* (2006.01)
- *C07C 11/08* (2006.01)
- *C10B 55/00* (2006.01)
- *C10G 9/36* (2006.01)
- *C10G 11/20* (2006.01)
- *C10G 21/00* (2006.01)
- *C10G 49/22* (2006.01)
- *C10G 69/14* (2006.01)

(52) U.S. Cl.
CPC .............. *C07C 11/08* (2013.01); *C10B 55/00* (2013.01); *C10G 9/36* (2013.01); *C10G 11/20* (2013.01); *C10G 21/003* (2013.01); *C10G 49/22* (2013.01); *C01B 2203/065* (2013.01); *C01B 2203/1241* (2013.01); *C10G 2300/1033* (2013.01); *C10G 2300/301* (2013.01); *C10G 2300/4006* (2013.01); *C10G 2300/4012* (2013.01); *C10G 2300/4018* (2013.01); *C10G 2300/4081* (2013.01); *C10G 2300/42* (2013.01); *C10G 2400/20* (2013.01); *C10G 2400/30* (2013.01)

(58) Field of Classification Search
CPC .......... C10G 67/0454; C10G 2300/206; C10G 2300/308; C10G 2300/4006; C10G 2300/4012; C10G 2400/30; C10G 2400/20; C07C 5/333; C07C 11/08; C07C 11/06
See application file for complete search history.

(56) References Cited

U.S. PATENT DOCUMENTS

| | | | |
|---|---|---|---|
| 3,702,292 A | 11/1972 | Burich | |
| 3,775,293 A | 11/1973 | Watkins | |
| 3,784,463 A | 1/1974 | Reynolds et al. | |
| 4,111,793 A | 9/1978 | Kolombos et al. | |
| 6,660,158 B1 | 12/2003 | Ellingsen | |
| 6,740,788 B1 | 5/2004 | Maher et al. | |
| 7,491,315 B2 | 2/2009 | Eng et al. | |
| 8,631,311 B1 | 1/2014 | Chan et al. | |
| 8,685,232 B2 | 4/2014 | Mandal et al. | |
| 9,228,140 B2 | 1/2016 | Abba et al. | |
| 10,316,258 B2 | 6/2019 | Rispoli et al. | |
| 10,407,630 B2 | 9/2019 | Al-Ghamdi et al. | |
| 10,472,580 B2 | 11/2019 | Al-Ghamdi et al. | |
| 10,717,941 B2 | 7/2020 | Al-Ghamdi et al. | |
| 11,242,493 B1 | 2/2022 | Xu et al. | |
| 2006/0042999 A1 | 3/2006 | Iqbal et al. | |
| 2008/0223754 A1 | 9/2008 | Subramanian et al. | |
| 2009/0143631 A1 | 6/2009 | Gracey et al. | |
| 2009/0294328 A1 | 12/2009 | Iqbal | |
| 2010/0037909 A1 | 2/2010 | Gross et al. | |
| 2010/0317909 A1 | 12/2010 | Keyvanloo et al. | |
| 2013/0112593 A1 | 5/2013 | Montanari et al. | |
| 2013/0248419 A1 | 9/2013 | Abba et al. | |
| 2016/0369189 A1 | 12/2016 | Ward et al. | |
| 2018/0142167 A1 | 5/2018 | Al-Ghamdi et al. | |
| 2018/0155633 A1 | 6/2018 | Al-Ghamdi et al. | |
| 2018/0291288 A1 | 10/2018 | Brown et al. | |
| 2018/0305623 A1 | 10/2018 | Al-Ghrami et al. | |
| 2020/0115645 A1 | 4/2020 | Al-Ghamdi et al. | |
| 2020/0392055 A1 | 12/2020 | Nesterenko et al. | |
| 2021/0087476 A1 | 3/2021 | Boualleg et al. | |
| 2021/0139793 A1 | 5/2021 | Al-Shafei et al. | |
| 2022/0017829 A1 | 1/2022 | Al-Shafei et al. | |
| 2022/0064546 A1 | 3/2022 | Al-Ghrami et al. | |
| 2022/0064548 A1 | 3/2022 | Akah et al. | |
| 2022/0064556 A1 | 3/2022 | Akah et al. | |

OTHER PUBLICATIONS

Akah et al., "An Overview of Light Olefins Production via Steam Enhanced Catalytic Cracking", Catalysis Surveys from Asia, vol. 23, pp. 265-276, 2019.

U.S. Office Action dated Mar. 24, 2023 pertaining to U.S. Appl. No. 17/865,995, filed Jul. 15, 2022, pp. 1-21.

U.S. Office Action dated Mar. 27, 2023 pertaining to U.S. Appl. No. 17/866,029, filed Jul. 15, 2022, pp. 1-22.

U.S. Office Action dated Mar. 27, 2023 pertaining to U.S. Appl. No. 17/866,035, filed Jul. 15, 2022, pp. 1-21.

US Office Action dated Apr. 14, 2023 pertaining to U.S. Appl. No. 17/865,787, filed Jul. 15, 2022, pp. 1-24.

METHODS FOR PROCESSING A HYDROCARBON OIL FEED STREAM UTILIZING A DELAYED COKER AND STEAM ENHANCED CATALYTIC CRACKER

TECHNICAL FIELD

Embodiments of the present disclosure generally relate to refining and upgrading hydrocarbon oil, and pertain particularly to an integrated process and system for upgrading a hydrocarbon oil stream, including heavy hydrocarbon residuals.

BACKGROUND

Olefins and aromatic compounds, such as ethylene, propylene, butylene, butadiene, benzene, toluene, and xylenes, are basic intermediates for many petrochemical industries. These olefins and aromatic compounds are usually obtained through the thermal cracking (or steam pyrolysis) of petroleum gases and distillates such as naphtha, kerosene, or gas oil. These compounds are also produced through refinery fluidized catalytic cracking (FCC) process where standard heavy feedstocks, such as gas oils or residues, are converted. Typical FCC feedstocks range from hydrocracked bottoms to heavy feed fractions, such as vacuum gas oil and atmospheric residue. However, these feedstocks are limited. Another source for propylene production is currently refinery propylene from FCC units. With the ever-growing demand, FCC unit owners look increasingly to the petrochemicals market to boost their revenues by taking advantage of economic opportunities that arise in the propylene market.

The worldwide increasing demand for light olefins remains a major challenge for many integrated refineries. In particular, the production of some valuable light olefins such as ethylene, propylene, and butylene has attracted increased attention as pure olefin streams are considered the building blocks for polymer synthesis. The production of light olefins depends on several process variables like the feed type, operating conditions, and the type of catalyst.

SUMMARY

Despite the options available for producing a greater yield of propylene and other light olefins, intense research activity in this field is still being conducted. Further, it is also desirable to produce light olefins and/or benzene, toluene, and xylenes, collectively referred to as "BTX," directly from a crude oil source. However, such methods may be problematic since crude oils often contain heavy residual hydrocarbons and other impurities that may interfere with the refining process, for example, in hydrocracking, steam cracking, and fluid catalytic cracking.

For example, these heavy residual hydrocarbons, such as asphaltenes, may affect the previous processes by generating a large amount of petroleum coke on catalysts used in the said refining processes. This buildup of coke may deactivate the catalysts used, resulting in increased costs to recycle or replace said deactivated catalysts or lowered light olefin and BTX conversion rates. The impurities may also negatively impact the said refining processes by lowering their efficiencies. The negative effects of nitrogen as an impurity in refining processes is well-known, contributing to a variety of problems such as, but not limited to, gum formation, catalyst inhibition and deactivation, acid-base pair-related corrosion, metal complexation, or combinations thereof.

Therefore, it may be desirable to initially treat a crude oil stream to upgrade heavy residual hydrocarbons and remove impurities before the crude oil stream is refined to avoid these negative effects. Furthermore, it may be desirable to further refine the upgraded heavy residual hydrocarbons to fully utilize the crude oil stream into light olefins and BTX.

Described herein are integrated processes and systems for producing light olefins (e.g., $C_2$-$C_4$ olefins) and/or BTX from crude oils, while providing the aforementioned benefits. Heavy hydrocarbons residuals such as asphaltenes may be upgraded in a solvent deasphalting unit and delayed coker to produce crude oil fractions upgradeable to light olefins and BTX, as well as disposable petroleum coke. These crude oil fractions may then be refined in a hydrotreater and separated into at least four fractions, which are separately processed. $C_{5+}$ hydrocarbon fractions may then be processed in steam enhanced catalytic crackers to produce olefins and BTX. $C_3$-$C_4$ hydrocarbon fractions may also be processed in a dehydrogenation unit to produce propylene and butylene. In this way, the entire crude oil is utilized to produce at least olefins, BTX, and petroleum coke.

In accordance with one embodiment herein, an integrated process for upgrading a hydrocarbon oil feed stream includes solvent deasphalting a hydrocarbon oil stream to form at least a deasphalted oil stream and heavy residual hydrocarbons, the heavy residual hydrocarbons including at least asphaltenes; delayed coking the heavy residual hydrocarbons to form petroleum coke and a delayed coker product stream; hydrotreating the delayed coker product stream and the deasphalted oil stream to form a $C_3$-$C_4$ hydrocarbon stream, a light $C_{5+}$ hydrocarbon stream, and a heavy $C_{5+}$ hydrocarbon stream; dehydrogenating the $C_3$-$C_4$ hydrocarbon stream to form propylene and butylene; steam enhanced catalytically cracking the light $C_{5+}$ hydrocarbon stream to form a light steam enhanced catalytically cracked product stream including olefins, benzene, toluene, xylene, naphtha, or combinations thereof; and steam enhanced catalytically cracking the heavy $C_{5+}$ hydrocarbon stream to form a heavy steam enhanced catalytically cracked product stream including olefins, benzene, toluene, xylene, naphtha, or combinations thereof.

According to another embodiment herein, an integrated system for the conversion of hydrocarbon oil feed streams includes a solvent deasphalting unit that separates a hydrocarbon oil stream into at least a deasphalted oil stream and heavy residual hydrocarbons, the heavy residual hydrocarbons including at least asphaltenes; a delayed coker fluidly connected to the solvent deasphalting unit that de-cokes the heavy residual hydrocarbons into at least a petroleum coke and a delayed coker product stream; a hydrotreater fluidly connected to the solvent deasphalting unit and the delayed coker that hydrotreats at least the deasphalted oil stream and the delayed coker product stream to form a $C_3$-$C_4$ hydrocarbon stream, a light $C_{5+}$ hydrocarbon stream and a heavy $C_{5+}$ hydrocarbon stream; a dehydrogenation unit fluidly connected to the hydrotreater and configured to dehydrogenate the $C_3$-$C_4$ hydrocarbon stream to form propylene and butylene; a first steam enhanced catalytic cracker fluidly connected to the hydrotreater that cracks at least a portion of the light $C_{5+}$ hydrocarbon fraction to form a light steam enhanced catalytically cracked product; and a second steam enhanced catalytic cracker fluidly connected to the hydrotreater that is in parallel with the first steam enhanced catalytic cracker, and that cracks at least a portion of the heavy $C_{5+}$ hydrocarbon fraction to form a heavy steam enhanced catalytically cracked product.

Additional features and advantages of the embodiments described herein will be set forth in the detailed description which follows, and in part will be readily apparent to those skilled in the art from that description or recognized by practicing the embodiments described, including the detailed description and the claims which are provided infra.

BRIEF DESCRIPTION OF THE DRAWINGS

The following detailed description of specific embodiments of the present disclosure can be best understood when read in conjunction with the following drawings in which.

Figure 1:
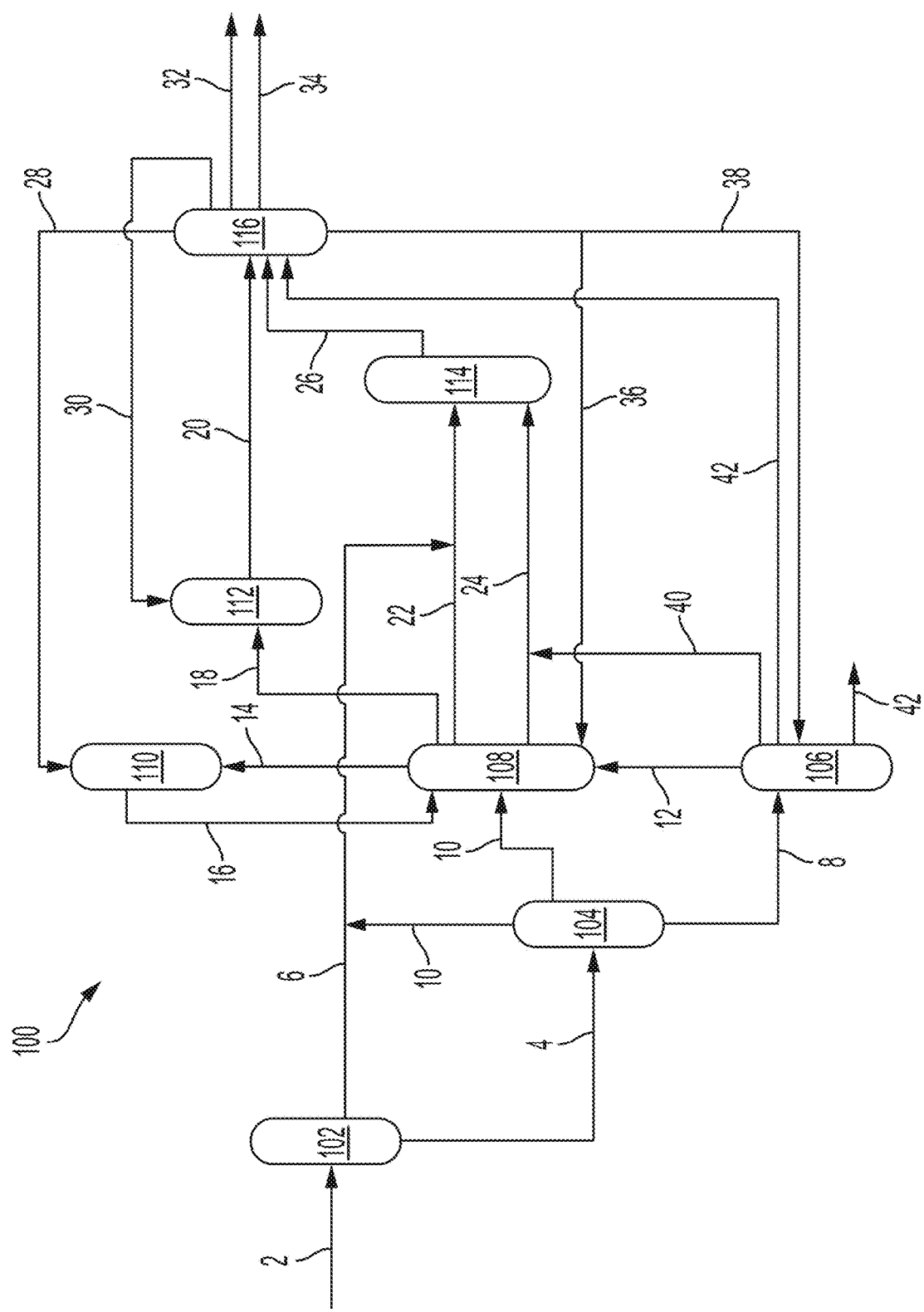
FIG. 1 illustrates a process flow diagram for an exemplary process in accordance with embodiments described herein.

For the purpose of describing the simplified schematic illustrations and descriptions of the relevant figures, the numerous valves, temperature sensors, electronic controllers and the like that may be employed and well known to those of ordinary skill in the art of certain chemical processing operations are not included. Further, accompanying components that are often included in typical chemical processing operations, such as air supplies, catalyst hoppers, and flue gas handling systems, are not depicted. Accompanying components that are in hydrotreating units, such as bleed streams, spent catalyst discharge subsystems, and catalyst replacement sub-systems are also not shown. It should be understood that these components are within the spirit and scope of the present embodiments disclosed. However, operational components, such as those described in the present disclosure, may be added to the embodiments described in this disclosure.

It should further be noted that arrows in the drawings refer to process streams. However, the arrows may equivalently refer to transfer lines, which may serve to transfer process streams between two or more system components. Additionally, arrows that connect to system components define inlets or outlets in each given system component. The arrow direction corresponds generally with the major direction of movement of the materials of the stream contained within the physical transfer line signified by the arrow. Furthermore, arrows, which do not connect two or more system components, signify a product stream, which exits the depicted system, or a system inlet stream, which enters the depicted system. Product streams may be further processed in accompanying chemical processing systems or may be commercialized as end products. System inlet streams may be streams transferred from accompanying chemical processing systems or may be non-processed feedstock streams. Some arrows may represent recycle streams, which are effluent streams of system components that are recycled back into the system. However, it should be understood that any represented recycle stream, in some embodiments, may be replaced by a system inlet stream of the same material, and that a portion of a recycle stream may exit the system as a product.

Additionally, arrows in the drawings may schematically depict process steps of transporting a stream from one system component to another system component. For example, an arrow from one system component pointing to another system component may represent "passing" a system component effluent to another system component, which may include the contents of a process stream "exiting" or being "removed" from one system component and "introducing" the contents of that product stream to another system component.

It should be understood that according to the embodiments presented in the relevant figures, an arrow between two system components may signify that the stream is not processed between the two system components. In other embodiments, the stream signified by the arrow may have substantially the same composition throughout its transport between the two system components. Additionally, it should be understood that in embodiments, an arrow may represent that at least 75 wt. %, at least 90 wt. %, at least 95 wt. %, at least 99 wt. %, at least 99.9 wt. %, or even 100 wt. % of the stream is transported between the system components. As such, in embodiments, less than all of the stream signified by an arrow may be transported between the system components, such as if a slip stream is present.

It should be understood that two or more process streams are "mixed" or "combined" when two or more lines intersect in the schematic flow diagrams of the relevant figures. Mixing or combining may also include mixing by directly introducing both streams into a like reactor, separation unit, or other system component. For example, it should be understood that when two streams are depicted as being combined directly prior to entering a separation unit or reactor, that in embodiments the streams could equivalently be introduced into the separation unit or reactor and be mixed in the reactor. Alternatively, when two streams are depicted to independently enter a system component, they may in embodiments be mixed together before entering that system component.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

Embodiments of the present disclosure are directed to integrated processes and systems for producing light olefins (e.g., $C_2$-$C_4$ olefins) and/or BTX from crude oils, while providing the aforementioned benefits.

As used herein, "asphaltenes" refers generally to the heaviest and most polar compounds naturally occurring in crude oil. Asphaltenes are a mixture of high molecular weight polycyclic aromatic hydrocarbons and heterocyclic compounds, primarily including carbon, hydrogen, nitrogen, oxygen, and sulfur, as well as trace amounts of vanadium and nickel. In asphaltenes, the hydrogen-to-carbon atomic ratio is approximately 1.2:1.0. Asphaltenes are generally n-pentane or n-heptane-insoluble, but toluene-soluble, and are generally a sticky, black, highly viscous residue of distillation processes.

As used herein, a "catalyst" refers to any substance that increases the rate of a specific chemical reaction. Catalysts described in this disclosure may be utilized to promote various reactions, such as, but not limited to, cracking (including aromatic cracking), demetalization, desulfurization, and denitrogenation. As used herein, "cracking" generally refers to a chemical reaction where carbon-carbon bonds are broken. For example, a molecule having carbon to carbon bonds is broken into more than one molecule by the breaking of one or more of the carbon to carbon bonds, or is converted from a compound which includes a cyclic moiety, such as a cycloalkane, cycloalkane, naphthalene, an aromatic or the like, to a compound which does not include a cyclic moiety or contains fewer cyclic moieties than prior to cracking.

As used herein, the term "crude oil" is to be understood to mean a mixture of petroleum liquids, gases, or combinations of liquids and gases, including some impurities such as sulfur-containing compounds, nitrogen-containing compounds and metal compounds that have not undergone significant separation or reaction processes. Crude oils are distinguished from fractions of crude oil. As used herein, the crude oil may be a minimally treated crude oil to provide a hydrocarbon oil feedstock having total metals (Nickel+Vanadium) content of less than 5 parts per million by weight (ppmw) and Conradson carbon residue of less than 5 wt. %. Such minimally treated materials may be considered crude oils as described herein.

As used herein, "distillate" refers to a crude oil fraction that includes $C_{5+}$ hydrocarbons with boiling points of between 204° C. and 343° C. Distillate may also be primarily composed of diesel and kerosene.

It should be understood that an "effluent" generally refers to a stream that exits a system component such as a separation unit, a reactor, or reaction zone, following a particular reaction or separation, and generally has a different composition (at least proportionally) than the stream that entered the separation unit, reactor, or reaction zone.

As used herein, "heavy cycle oil" refers to a hydrocarbon crude oil fraction that includes $C_{5+}$ hydrocarbons with boiling points of between 426° C. and 640° C. "Light cycle oil," as used herein, refers to a crude oil fraction that includes $C_{5+}$ hydrocarbons with boiling points of between 343° C. and 426° C.

As used herein, the terms "hourly space velocity," "gas hourly space velocity," and "liquid hourly space velocity" may collectively refer to the rate at which a feed stream travels through the treatment units, reactors, and separators discussed herein. Further, hourly space velocity may also be inversely proportional to the residence time for the same, i.e. residence time may be expressed as one over the hourly space velocity. "Residence time," as used herein, refers to the amount of time taken for a feed stream to enter and then exit the treatment units, reactors, and separators discussed herein.

As used herein, the term "naphtha" refers to a mixture of substances primarily including $C_5$ to $C_{11}$ hydrocarbons. "Light naphtha," as used herein, is a fraction of naphtha primarily including $C_5$ to $C_6$ hydrocarbons. As used herein, the term "heavy naphtha" refers to a fraction of naphtha primarily including $C_7$ to $C_{11}$ hydrocarbons.

As used herein, the term "steam/oil ratio" or "steam-to-oil ratio" or "steam-to-hydrocarbon oil ratio" or "steam-to-feed ratio" refers to a standard measure of the volume rate of steam circulating through the reactor with respect to the volume of feed. The steam/oil ratio may be determined by comparing the flow volume of a steam stream and the flow volume of a hydrocarbon oil feed or the flow volume of a second steam stream and the flow volume of a hydrocarbon product stream.

As used herein, a "reactor" refers to a vessel in which one or more chemical reactions may occur between one or more reactants optionally in the presence of one or more catalysts. For example, a reactor may include a tank or tubular reactor configured to operate as a batch reactor, a continuous stirred-tank reactor (CSTR), or a plug flow reactor. Exemplary reactors include packed bed reactors such as fixed-bed reactors, and fluidized bed reactors. One or more "reaction zones" may be disposed in a reactor. As used herein, a "reaction zone" refers to an area where a particular reaction takes place in a reactor. For example, a packed bed reactor with multiple catalyst beds may have multiple reaction zones, where each reaction zone is defined by the area of each catalyst bed.

As used herein, a "separation unit" or "separator" refers to any separation device that at least partially separates one or more chemicals that are mixed in a process stream from one another. For example, a separation unit may selectively separate differing chemical species, phases, or sized material from one another, forming one or more chemical fractions. Examples of separation units include, without limitation, distillation columns, flash drums, knock-out drums, knock-out pots, centrifuges, cyclones, filtration devices, traps, scrubbers, expansion devices, membranes, solvent extraction devices, and the like. It should be understood that separation processes described in this disclosure may not completely separate all of one chemical constituent from all of another chemical constituent. It should be understood that the separation processes described in this disclosure "at least partially" separate different chemical components from one another, and that even if not explicitly stated, it should be understood that separation may include only partial separation. As used herein, one or more chemical constituents may be "separated" from a process stream to form a new process stream. Generally, a process stream may enter a separation unit and be divided, or separated, into two or more process streams of desired composition. Further, in some separation processes, a "lower boiling point fraction" (sometimes referred to as a "light fraction" or "light fraction stream") and a "higher boiling point fraction" (sometimes referred to as a "heavy fraction," "heavy hydrocarbon fraction," or "heavy hydrocarbon fraction stream") may exit the separation unit, where, on average, the contents of the lower boiling point fraction stream have a lower boiling point than the higher boiling point fraction stream. Other streams may fall between the lower boiling point fraction and the higher boiling point fraction, such as a "medium boiling point fraction."

It should further be understood that streams may be named for the components of the stream, and the component for which the stream is named may be the major component of the stream (such as including from 50 weight percent (wt. %), from 70 wt. %, from 90 wt. %, from 95 wt. %, from 99 wt. %, from 99.5 wt. %, or even from 99.9 wt. % of the contents of the stream to 100 wt. % of the contents of the stream). It should also be understood that components of a stream are disclosed as passing from one system component to another when a stream comprising that component is disclosed as passing from that system component to another. By way of non-limiting example, a referenced "$C_2$-$C_4$ hydrocarbon stream" passing from a first system component to a second system component should be understood to equivalently disclose "$C_2$-$C_4$ hydrocarbons" passing from a first system component to a second system component, and the like.

Referring initially to FIG. 1, an integrated system 100 for the conversion of hydrocarbon oil feedstocks is illustrated. As used herein, "feed stock" may also be used to refer to "feed stream(s)." The integrated system 100 includes a solvent deasphalting unit 104, a delayed coker 106, a hydrotreater 108, and steam enhanced catalytic crackers 114. While FIG. 1 appears to show only one steam enhanced catalytic cracker, it should be understood that 114 is meant to illustrate multiple steam enhanced catalytic crackers, particularly a first steam enhanced catalytic cracker and a second steam enhanced catalytic cracker, together encompassing the steam enhanced catalytic crackers 114. The illustration of one steam enhanced catalytic cracker for 114 is meant for simplification of the flow patterns of FIG. 1.

Further, it should be understood that the use of "light" and "heavy" as identifiers for the steam enhanced catalytic crackers 114 are used simply for the purpose of referencing the feed streams that may enter the steam enhanced catalytic crackers 114. For example, the light steam enhanced catalytic cracker may be understood to have lighter hydrocarbon feeds that have lower boiling points than the feeds for heavy steam enhanced catalytic cracker. Similarly, the heavy steam enhanced catalytic cracker may be understood to have heavier hydrocarbon feeds that have higher boiling points than the feeds for the light steam enhanced catalytic cracker.

Still referring to FIG. 1, the solvent deasphalting unit 104 separates a hydrocarbon oil stream 2 into at least a deasphalted oil stream 10 and heavy residual hydrocarbons 8. The heavy residual hydrocarbons 8 may include at least asphaltenes in the form of a pitch. In embodiments, the solvent deasphalting unit may include a solvent. The solvent may be a light paraffinic hydrocarbon, such as, but not limited to n-propane, n-butane, n-pentane, n-hexane, n-heptane, or combinations thereof. In embodiments, the heavy residual hydrocarbons 8 may further include non-hydrocarbon constituents and impurities. In this way, the solvent deasphalting unit 104 may remove asphaltenes, non-hydrocarbon constituents, impurities, or combinations thereof, from the hydrocarbon oil stream 2 to form the deasphalted oil stream 10. For example, the solvent deasphalting unit 104 may remove nitrogen-containing compounds, sulfur-containing compounds, Conradson carbon residue (CCR), and metal compounds such as nickel and vanadium. In embodiments, removing non-hydrocarbon constituents and impurities like the immediately previous may increase the efficiency of downstream treatment units by reducing the coking deactivation rate of the various catalysts used therein.

In embodiments, the solvent deasphalting unit 104 may be operated at a temperature of from 40° C. to 100° C., from 40° C. to 90° C., from 40° C. to 70° C., from 40° C. to 60° C., from 60° C. to 100° C., from 60° C. to 90° C., from 60° C. to 70° C., from 70° C. to 100° C., from 70° C. to 90° C., or from 90° C. to 100° C. The solvent deasphalting unit 104 may be operated at a pressure of from 0.1 MPa to 0.4 MPa.

Still referring to FIG. 1, the delayed coker 106 is fluidly connected to the solvent deasphalting unit 104 and de-cokes the heavy residual hydrocarbons 8 into at least a petroleum coke 42 and a delayed coker product stream 12. As used herein, "de-coke," may also refer to "delayed coking," i.e. the delayed coker 106 may de-coke, or remove coke from, an input stream. In embodiments, de-coking the heavy residual hydrocarbons 8 may allow the further upgrading of the heavy residual hydrocarbons 8 into the desired product streams, namely olefins and BTX. This may increase the total volume of usable oil and hydrocarbon products recovered from the hydrocarbon oil stream 2. Removing the petroleum coke 42 from the heavy residual hydrocarbons 8 may also reduce the amount of coke precursors present in the delayed coker product stream 12. Removal of the coke precursors may also reduce the coking deactivation rate of the various catalysts used in the downstream treatment units discussed herein. As used herein, "coke precursors" are crude oil fractions that are generally known to have a tendency to form coke on catalysts during crude oil refining, thus increasing the catalysts' deactivation rate.

The delayed coker 106 may also produce hydrogen as a by-product of the delayed coking reactions. It is contemplated that the hydrogen generated by the delayed coker 106 may have the additional benefit of at least partially reducing the need for external sources of hydrogen for the hydrotreater 108. In one non-limiting example, operating the delayed coker 106 within the operating ranges disclosed herein may produce 0.1 wt. % hydrogen by weight of the delayed coker product stream 12.

In embodiments, the delayed coker 106 may be operated at a temperature of less than or equal to 600° C., less than or equal to 550° C., less than or equal to 500° C., or even less than or equal to 485° C. The delayed coker 106 may be operated at a temperature of from 450° C. to 600° C., from 450° C. to 550° C., from 450° C. to 500° C., from 450° C. to 485° C., from 485° C. to 600° C., from 485° C. to 550° C., from 485° C. to 500° C., from 500° C. to 600° C., from 500° C. to 550° C., or from 550° C. to 600° C. The delayed coker 106 may be operated at a pressure of from MPa to 0.4 MPa.

In embodiments, and as illustrated in FIG. 1, the delayed coker 106 may also be fluidly connected to the steam enhanced catalytic crackers 114, a final product separator 116, or both. In embodiments where the hydrotreater 108 is disabled or down-for-repairs, the delayed coker 106 may send the delayed coker product stream 12 directly to the steam enhanced catalytic crackers 114, the final product separator 116, or both. This may include, in particular, the delayed coker 106 sending the delayed coker product stream 12 to the second steam enhanced catalytic cracker. In embodiments, this may allow the direct conversion of the delayed coker product stream 12 into the light steam enhanced catalytic cracker product stream.

Still referring to FIG. 1, and in embodiments, hydrocarbon oil stream 2 may include whole crude oil, topped crude oil, or a combination thereof. Whole crude oil may include crude oil as previously described. As described herein, "topped crude oil" is understood to mean a fraction of crude oil with boiling points less than 160° C. While the present description and examples may specify hydrocarbon oil as the feedstock stream, it should be understood that the systems 100 and 200, described with respect to the embodiments of FIGS. 1 and 2, may be applicable for the conversion of a wide variety of crude oils, which may be present in the hydrocarbon oil stream 2. The hydrocarbon oil stream 2 may include one or more non-hydrocarbon constituents, such as one or more heavy metals, sulfur compounds, nitrogen compounds, inorganic components, or other non-hydrocarbon compounds.

In embodiments, hydrocarbon oil stream 2 may be a heavy crude oil, which includes crude oil having an American Petroleum Institute (API) gravity of less than 35°, 34.5°, 34°, or 33°. In these embodiments, the crude oil may have a sulfur content of greater than or equal to 1.5 weight percent (wt. %), based on the total weight of the crude oil, such as greater than or equal to 1.6 wt. %, 1.7 wt. %, 1.75 wt. %, 1.8 wt. %, 1.9 wt. %, or 2.0 wt. %. By way of non-limiting example, the hydrocarbon oil stream 2 may be Arab Heavy crude oil, which has an API gravity of approximately 28° and a sulfur content of approximately 2.8 wt. %. In embodiments, the hydrocarbon oil stream 2 may be a light crude oil, which includes crude oil having an American Petroleum Institute (API) gravity of greater than 35°, 36°, 37°, or 38°. In these embodiments, the light crude oil may also be categorized as a sour light crude oil, which includes crude oil having a sulfur content of less than 1.5 weight percent (wt. %), based on the total weight of the crude oil, such as less than or equal to 1.4 wt. %, 1.3 wt. %, 1.2 wt. %, 1.1 wt. %, or 1.0 wt. %. By way of non-limiting example, the hydrocarbon oil stream 2 may be Arab Light crude oil, which has an API gravity of approximately 33° and a sulfur content of approximately 1.77 wt. %. By way of another non-limiting example, the hydrocarbon oil stream 2 may be Arab Extra Light crude oil, which has an API gravity of approximately 39° and a sulfur content of approximately 1.1 wt. %. In embodiments, the hydrocarbon oil stream 2 may be a combination of crude oils, such as, for example, a combination of Arab Light crude oil and Arab Extra Light crude oil. It should be understood that, as used herein, the "hydrocarbon oil stream" may refer to crude oil, which has not been previously treated, separated, or otherwise refined. Table 1 below set forth properties of an Arab light crude oil, as may be used in embodiments, herein.

TABLE 1

Arab Light Crude Oil Composition

| Property | Arab Light Crude |
|---|---|
| Density | 0.8537 |
| S (ppmw) | 1.94 |
| N (ppmw) | 830 |
| Ni (ppmw) | 3.1 |
| V (ppmw) | 10.2 |
| Na (ppmw) | 0.9 |
| Conradson Carbon (wt. %) | 4.25 |

In embodiments, the hydrocarbon oil stream 2 may have a density lower than 0.89 g/mL. In embodiments, the hydrocarbon oil stream 2 may have a density of from 0.75 g/mL to 0.92 g/mL, from 0.75 g/mL to 0.89 g/mL, from 0.75 g/mL to 0.87 g/mL, from 0.75 g/mL to 0.84 g/mL, from 0.84 g/mL to 0.92 g/mL, from 0.84 g/mL to 0.89 g/mL, from 0.84 g/mL to 0.87 g/mL, from 0.87 g/mL to 0.92 g/mL, from 0.87 g/mL to 0.89 g/mL, or from 0.89 g/mL to 0.92 g/Ml.

In embodiments including Arab extra light crude oil, the hydrocarbon oil stream 2 may have 44.9 wt. % of greater than 300° C. boiling point hydrocarbon fractions, as measured by the total weight of the hydrocarbon oil stream 2. The hydrocarbon oil stream may have 52.7 wt. % of less than or equal to 300° C. boiling point hydrocarbon fractions, as measured by the total weight of the hydrocarbon oil stream 2. The hydrocarbon oil stream 2 may also have a remainder of non-hydrocarbon constituents. In embodiments including Arab light crude oil, the hydrocarbon oil stream 2 may have 55.69 wt. % of greater than 300° C. boiling point hydrocarbon fractions, as measured by the total weight of the hydrocarbon oil stream 2. The hydrocarbon oil stream may have of 44.31 wt. % less than or equal to 300° C. boiling point hydrocarbon fractions, as measured by the total weight of the hydrocarbon oil stream 2. The hydrocarbon oil stream 2 may also have a remainder of non-hydrocarbon constituents. In embodiments including Arab light crude oil, the hydrocarbon oil stream 2 may have 66.1 wt. % of greater than 300° C. boiling point hydrocarbon fractions, as measured by the total weight of the hydrocarbon oil stream 2. The hydrocarbon oil stream may have of 32.4 wt. % less than or equal to 300° C. boiling point hydrocarbon fractions, as measured by the total weight of the hydrocarbon oil stream 2. The hydrocarbon oil stream 2 may also have a remainder of non-hydrocarbon constituents.

In embodiments, the hydrocarbon oil stream 2 may have from 1 wt. % to 20 wt. %, from 1 wt. % to 16 wt. %, from 1 wt. % to 14 wt. %, from 1 wt. % to 10 wt. %, from 1 wt. % to 8 wt. %, from 1 wt. % to 4 wt. %, from 4 wt. % to 20 wt. %, from 4 wt. % to 16 wt. %, from 4 wt. % to 14 wt. %, from 4 wt. % to 10 wt. %, from 4 wt. % to 8 wt. %, from 8 wt. % to 20 wt. %, from 8 wt. % to 16 wt. %, from 8 wt. % to 14 wt. %, from 8 wt. % to 10 wt. %, from 10 wt. % to 20 wt. %, from 10 wt. % to 16 wt. %, from 10 wt. % to 14 wt. %, from 14 wt. % to 20 wt. %, from 14 wt. % to 16 wt. %, or from 16 wt. % to 20 wt. % of >540° C. boiling point hydrocarbon fractions.

In embodiments, the heavy residual hydrocarbons 8 may include $C_{5+}$ hydrocarbons having boiling points of between 426° C. to 650° C. As mentioned earlier, the heavy residual hydrocarbons 8 may be a pitch product including, in part, asphaltenes. The heavy residual hydrocarbons may also be atmospheric residue oil, vacuum residual oil, or both. In embodiments, the deasphalted oil stream 10 may include $C_1$ to $C_{5+}$ hydrocarbons having boiling points of between −162° C. to 650° C.

In embodiments, the delayed coker product stream 12 may include $C_{5+}$ hydrocarbons having boiling points of between 350° C. to 650° C. The delayed coker product stream 12 may be naphtha, gas oil, or both. The petroleum coke 12 may be needle coke, sponge coke, honeycomb coke, shot coke, or combinations thereof. The petroleum coke 12 may be primarily composed of carbon, along with lesser amounts of non-hydrocarbon constituents. The petroleum coke may also be primarily composed of $C_{5+}$ hydrocarbons having boiling points of greater than 650° C.

Still referring to FIG. 1, the hydrotreater 108 is fluidly connected to the solvent deasphalting unit 104 and the delayed coker 106 and hydrotreats at least the deasphalted oil stream 10 and the delayed coker product stream 12 to form a light $C_{5+}$ hydrocarbon stream 22 and a heavy $C_{5+}$ hydrocarbon stream 24. In embodiments, the hydrotreater may also hydrotreat at least the deasphalted oil stream 10 and the delayed coker product stream 12 to additionally form a $C_1$ hydrocarbon stream 14 and a $C_2$-$C_4$ hydrocarbon stream 18. In embodiments, the $C_1$ hydrocarbon stream, the $C_2$-$C_4$ hydrocarbon stream, the light $C_{5+}$ hydrocarbon stream, and the heavy $C_{5+}$ hydrocarbon stream may collectively be referred to as a hydrotreated product stream. In additional embodiments, the hydrotreater may additionally form a $C_{9+}$ heavy residual hydrocarbon stream, which may be recycled back to the delayed coker to produce additional delayed coker product stream 12 and petroleum coke.

In embodiments, hydrotreater 108 may be operated at a temperature of from 370° C. to 500° C. The hydrotreater 108 may be operated at a temperature of from 370° C. to 500° C., from 370° C. to 480° C., from 370° C. to 450° C., from 370° C. to 420° C., from 370° C. to 400° C., from 370° C. to 390° C., from 370° C. to 380° C., from 380° C. to 500° C., from 380° C. to 480° C., from 380° C. to 450° C., from 380° C. to 420° C., from 380° C. to 400° C., from 380° C. to 390° C., from 390° C. to 500° C., from 390° C. to 480° C., from 390° C. to 450° C., from 390° C. to 420° C., from 390° C. to 400° C., from 400° C. to 500° C., from 400° C. to 480° C., from 400° C. to 450° C., from 400° C. to 420° C., from 420° C. to 500° C., from 420° C. to 480° C., from 420° C. to 450° C., 450° C. to 500° C., from 450° C. to 480° C., or from 480° C. to 500° C. The hydrotreater 108 may be operated at a pressure of from 0.1 MPa to 0.2 MPa.

In embodiments, the hydrotreater 108 may have a liquid hourly space velocity of from $0.2\ h^{-1}$ to $0.7\ h^{-1}$. The hydrotreater 108 may have a liquid hourly space velocity of from $0.2\ h^{-1}$ to $0.7\ h^{-1}$, from $0.2\ h^{-1}$ to $0.6\ h^{-1}$, from $0.2\ h^{-1}$ to $0.5\ h^{-1}$, from $0.2\ h^{-1}$ to $0.4\ h^{-1}$, from $0.2\ h^{-1}$ to $0.3\ h^{-1}$, from $0.3\ h^{-1}$ to $0.7\ h^{-1}$, from $0.3\ h^{-1}$ to $0.6\ h^{-1}$, from $0.3\ h^{-1}$ to $0.5\ h^{-1}$, from $0.3\ h^{-1}$ to $0.4\ h^{-1}$, from $0.4\ h^{-1}$ to $0.7\ h^{-1}$, from $0.4\ h^{-1}$ to $0.6\ h^{-1}$, from $0.4\ h^{-1}$ to $0.5\ h^{-1}$, from $0.5\ h^{-1}$ to $0.7\ h^{-1}$, from $0.5\ h^{-1}$ to $0.6\ h^{-1}$, or from $0.6\ h^{-1}$ to $0.7\ h^{-1}$.

In embodiments, the hydrotreater 108 may include a hydrotreating catalyst. The hydrotreating catalyst may include an active-phase metal on a support. The active-phase metal may include nickel, molybdenum, tungsten, platinum, palladium, rhodium, ruthenium, gold, or combinations thereof. In embodiments, the support may include amorphous alumina, crystalline silica-alumina, alumina, silica, and combinations thereof. The hydrotreating catalyst may include MoNi on $Al_2O_3$, MoCo on $Al_2O_3$, $MoS_2$, maghemite, $Fe_3O_4$, nickel, NiO, $TiO_2$, $ZrO_2$, $CeO_2$, or combinations thereof.

In embodiments, the $C_2$-$C_4$ hydrocarbon stream 18 may generally include $C_2$-$C_4$ hydrocarbons, including $C_2$-$C_4$ paraffins, $C_2$-$C_4$ olefins, $C_2$-$C_4$ alkynes, or combinations thereof. The $C_2$-$C_4$ hydrocarbon stream may include ethane, propane, butane, ethylene, propylene, butylene, ethyne, propyne, butyne, or combinations thereof. In embodiments, the light $C_{5+}$ hydrocarbon stream 22 may include $C_{5+}$ hydrocarbons having a having a $T_{95}$ boiling point (that is, the temperature at which greater than 95% of components are boiling in a hydrocarbon composition) of less than 200° C. The heavy $C_{5+}$ hydrocarbon stream 24 may include may include $C_{5+}$ hydrocarbons having a $T_5$ boiling point (that is, the temperature at which less than 5% of components are boiling in a hydrocarbon composition) of greater than or equal to 200° C. Accordingly, the temperature cut between the light $C_{5+}$ hydrocarbon stream 22 and the heavy $C_{5+}$ hydrocarbon stream 24 may be 200° C. However, the temperature cut between the light and heavy $C_{5+}$ hydrocarbon streams may also be greater or less than 200° C. depending upon the components in the hydrocarbon oil stream 2.

In embodiments, the heavy $C_{5+}$ hydrocarbon stream 24 may generally include hydrocarbon residues having an API gravity of at least 8.0° and/or a standard liquid density of at least 1,000 kilograms per cubic meter ($kg/m^3$). However, it is contemplated that the amount of hydrocarbon residue present in the heavy $C_{5+}$ hydrocarbon stream 24 may generally be dependent on the efficiency of the delayed coker 106.

As previously mentioned, the steam enhanced catalytic crackers 114 include the first steam enhanced catalytic cracker and the second steam enhanced catalytic cracker. The first steam enhanced catalytic cracker is fluidly connected to the hydrotreater 108 and cracks at least a portion of the light $C_{5+}$ hydrocarbon stream 22 to form a light steam enhanced catalytically cracked product 26. The second steam enhanced catalytic cracker is fluidly connected to the hydrotreater 108 and cracks at least a portion of the heavy $C_{5+}$ hydrocarbon stream 24 to form a heavy steam enhanced catalytically cracked product 28. The first and second steam enhanced catalytic crackers are in parallel to each other and downstream of the hydrotreater 108. In embodiments, the steam enhanced catalytic crackers may also be fluidly connected to the deasphalting unit 104. In this configuration, the deasphalting unit 104 may send at least a portion of the deasphalted oil stream to the steam enhanced catalytic crackers 114. In embodiments, the light steam enhanced catalytically cracked product stream 26, the heavy steam enhanced catalytically cracked product stream 28, or both may include olefins, BTX, naphtha, or combinations thereof. The olefins may include ethylene, propylene, butylene, or combinations thereof. In embodiments, the olefins may additionally include gasoline.

In embodiments, the light and heavy $C_{5+}$ hydrocarbon streams may need to be processed at different conditions in the steam enhanced catalytic crackers 114 to maximize the yield of desired products. In one non-limiting example, the light $C_{5+}$ hydrocarbon stream 22 may require a longer residence time than the heavy $C_{5+}$ hydrocarbon stream 24 to fully treat and convert the light components of the light $C_{5+}$ hydrocarbon stream 22. Additionally, the heavy $C_{5+}$ hydrocarbon stream 24 may require a shorter residence time to avoid excessive coking of the components of the heavy $C_{5+}$ hydrocarbon stream 24.

The first and second steam enhanced catalytic crackers may also generate different distributions of hydrocarbon products with their product streams. For example, the first steam enhanced catalytic cracker may generate a greater proportion of olefins than naphtha range products (including naphtha and gasoline). In embodiments, the first steam enhanced catalytic cracker may generate an olefin to naphtha product ratio of approximately 5.5:1 or of approximately 6.5:1 olefin to naphtha. The first steam enhanced catalytic cracker may also generate an olefin to naphtha product ratio of from 2:1, from 3:1, from 4:1, from 5:1, from 6:1, or from 7:1 olefins to naphtha.

Similarly, the second steam enhanced catalytic cracker may generate a greater proportion of naphtha and gasoline range products rather than olefins. In embodiments, the second steam enhanced catalytic cracker may generate an olefin to naphtha product ratio of approximately 8:9 or of approximately 3:4 olefin to naphtha. The second steam enhanced catalytic cracker may also generate an olefin to naphtha product ratio of from 1.5:1, from 1.3:1, from 1.1:1, from 1:1, from 0.9:1, or from 0.8:1 olefins to naphtha.

However, if two steam enhanced catalytic crackers are not available, the light $C_{5+}$ hydrocarbon stream 22 and the heavy $C_{5+}$ hydrocarbon stream 24 may be processed in one steam enhanced catalytic cracker at different conditions, but with different distributions of hydrocarbon products.

The steam enhanced catalytic crackers 114 may be a riser type or a downer type cracker. As used herein, "riser type" reactors or units are those that have feed enter at the bottom of the reactor and exit at the type. As used herein, "downer type" reactors or units are those that have feed enter at the top of the reactor and exit at the bottom. For riser type crackers, it is contemplated that the residence time will generally be longer than for downer type crackers due to back-mixing of the feed stream as it rises in the riser type cracker. Conversely, for downer type crackers, it is contemplated that the residence time will generally be shorter than for the riser type crackers because of the effect of gravity on the feed stream. Therefore, in embodiments, the first steam enhanced catalytic cracker may be a riser type cracker and the second steam enhanced catalytic cracker may be a downer type cracker to take advantage of the relative residence times of the two. However, any combination of type-crackers may be used herein, such as riser-riser, downer-downer, downer-riser, etc.

In embodiments, the steam enhanced catalytic crackers 114 may operate with a residence time of between 0.5 seconds to 10 seconds. The steam enhanced catalytic crackers 114 may operate with a residence time of from 0.1 seconds to 20 seconds, from 0.1 to 15 seconds, from 0.1 to 10 seconds, from 0.1 to 5 seconds, from 0.1 to 1 seconds, from 0.1 to 0.5 seconds, from 0.5 to 20 seconds, from 0.5 to 15 seconds, from 0.5 to 10 seconds, from 0.5 to 5 seconds, from 0.5 to 1 seconds, from 1 to 20 seconds, from 1 to 15 seconds, from 1 to 10 seconds, from 1 to 5 seconds, from 5 to 20 seconds, from 5 to 15 seconds, from 5 to 10 seconds, from 10 to 20 seconds, from 10 to 15 seconds, or from 15 seconds to 20 seconds. As previously mentioned, the residence times may be different for the first and second steam enhanced catalytic crackers. In embodiments, the first steam enhanced catalytic cracker may have a residence time of from 3 seconds to 10 seconds, or any of the narrower ranges therein. The second steam enhanced catalytic cracker may have a residence time of from 1 second to 3 seconds, or any of the narrower ranges therein.

In embodiments, the steam enhanced catalytic crackers 114 may be fixed bed catalytic cracking reactors that may include steam and a cracking catalyst disposed within a steam cracking catalyst zone. In embodiments, the steam enhanced catalytic crackers 114 may include a porous packing material, such as silica carbide packing, upstream of the steam cracking catalyst zone. The porous packing material may ensure sufficient heat transfer to the $C_{5+}$ hydrocarbon fractions and steam prior to conducting the steam enhanced catalytic cracking reaction in the steam cracking catalyst zone. Without being bound by theory, it is believed that a system that includes the steam enhanced catalytic cracking system 114 produces more light olefins compared to systems that incorporate conventional fluid catalytic cracking (FCC) units. Typically, FCC units are set up mainly to upgrade heavy feeds to gasoline and other transportation fuels. Further, typical FCC units are not set up to handle large quantities of steam like those used in steam enhanced catalytic cracking.

In embodiments, the cracking catalyst may be a nano-zeolite cracking catalyst including nano-zeolite particles. A variety of nano-zeolites may be suitable for the steam enhanced catalytic cracking reactions in the steam enhanced catalytic cracking reactors 114. The nano-zeolite cracking catalyst may include a structured zeolite, such as an MFI, a GIS, or a BEA structured zeolite, for example. In embodiments, the nano-zeolite cracking catalyst may include nano ZSM-5 zeolite, nano BEA zeolite, nano USY zeolite, combinations thereof. In embodiments, the nano-zeolite cracking catalyst may be loaded with phosphorous and a combination of heavy metals (e.g., metals having a density of greater than 5 $g/cm^3$), such as iron, lanthanum, cerium, zirconium, and combinations thereof. The nano-zeolites, such as nano-ZSM-S zeolite, nano Beta zeolite, nano USY, or combinations thereof may be in hydrogen form. In hydrogen form, the Brønsted acid sites in the zeolite, also known as bridging OH—H groups, may form hydrogen bonds with other framework oxygen atoms in the zeolite framework.

In embodiments, the nano ZSM-5 zeolite, the nano Beta zeolite, the nano USY zeolite, or combinations thereof may have a molar ratio of silica to alumina to provide sufficient acidity to the nano-zeolite cracking catalyst to conduct the steam enhanced catalytic cracking reactions. The nano ZSM-5 zeolite, the nano Beta zeolite, the nano USY zeolite, or combinations thereof may have a molar ratio of silica to alumina of from 10 to 200, from 15 to 200, from 20 to 200, from 10 to 150, from 15 to 150, or from 20 to 150. The nano ZSM-5 zeolite, the nano Beta zeolite, the nano USY zeolite, or combinations thereof may have total acidity in the range of 0.2 millimoles/gram (mmol/g) to 2.5 mmol/g, 0.3 mmol/g to 2.5 mmol/g, 0.4 mmol/g to 2.5 mmol/g, 0.5 mmol/g to 2.5 mmol/g, 0.2 mmol/g to 2.0 mmol/g, 0.3 mmol/g to 2.0 mmol/g, 0.4 mmol/g to 2.0 mmol/g, or 0.5 mmol/g to 2.0 mmol/g. The nano ZSM-5 zeolite, the nano Beta zeolite, the nano USY zeolite, or combinations thereof may have an average crystal size of from 50 nanometer (nm) to 600 nm, from 60 nm to 600 nm, from 70 nm to 600 nm, from 80 nm to 600 nm, from 50 nm to 580 nm, or from 50 nm to 550 nm.

The nano-zeolite cracking catalyst may also include an alumina binder, which may be used to consolidate the nanoparticles of nano ZSM-5 zeolite, nano Beta zeolite, nano USY zeolite, or combinations thereof to form the nano-zeolite cracking catalyst. The nano-zeolite cracking catalyst may be prepared by combining the nano ZSM-5 zeolite, the nano Beta zeolite, the nano USY zeolite, or combinations thereof with the aluminum binder and extruding the nano-zeolite cracking catalyst to form pellets or other catalyst shapes. The nano-zeolite cracking catalyst may include from 10 weight percent (wt. %) to 80 wt. %, from 10 wt. % to 75 wt. %, from 10 wt. % to 70 wt. %, from 15 wt. % to 80 wt. %, from 15 wt. % to 75 wt. %, or from 15 wt. % to 70 wt. % alumina binder based on the total weight of the nano-zeolite cracking catalyst. The nano-zeolite cracking catalyst may have a mesoporous to microporous volume ratio in the range of from 0.5 to 1.5, from 0.6 to 1.5, from 0.7 to 1.5, from 0.5 to 1.0, from 0.6 to 1.0, or from 0.7 to 1.0.

In embodiments, the steam in the steam enhanced catalytic cracker may reduce the hydrocarbon partial pressure, which may have the dual effects of increasing yields of light olefins and/or BTX hydrocarbons as well as reducing coke formation. Light olefins like propylene and butylene are mainly generated from catalytic cracking reactions following the carbonium ion mechanism, and as these are intermediate products, they can undergo secondary reactions such as hydrogen transfer and aromatization (leading to coke formation). The steam may increase the yield of light olefins by suppressing these secondary bi-molecular reactions, and reduce the concentration of reactants and products, which favor selectivity towards light olefins. The steam may also suppress secondary reactions that are responsible for coke formation on catalyst surface, which is good for catalysts to maintain high average activation. These factors may show that a large steam-to-oil weight ratio may be beneficial to the production of light olefins.

In embodiments, and as previously mentioned, increasing the steam-to-feed ratio may improve the light olefin yield of the steam enhanced catalytic cracker. A ratio of the flowrate (gas hourly space velocity) of steam to the flowrate (gas hourly space velocity) of the feed (light $C_{5+}$ hydrocarbon stream 22 or heavy $C_{5+}$ hydrocarbon stream 24) to the steam enhanced catalytic cracking reactors 114 may be from 0.1 to 1.1 times, from 0.1 to 0.8 times, from 0.1 to 0.5 times, from 0.1 to 0.2 times, from 0.2 to 1.1 times, from 0.2 to 0.8 times, from 0.2 to 0.5 times, from 0.5 to 1.1 times, from 0.5 to 0.8 times, or from 0.8 to 1.1 times steam to feed to improve the steam enhanced catalytic cracking process. In embodiments, the ratio of steam to feed may be different for the first steam enhanced catalytic cracker and the second steam enhanced catalytic cracker. For example, the second steam enhanced catalytic cracker may have a steam to feed ratio of from 0.8 to 1.0 steam to feed, whereas the first steam enhanced catalytic cracker may have a steam to feed ratio of from 0.2 to 0.8. In embodiments, the higher steam to feed ratio may be beneficial for the heavy fractions due to the need to reduce the viscosity of heavier crude oil fraction as well as atomize the heavy fractions.

In embodiments, the steam may be injected into the steam enhanced catalytic crackers 114 at a gas hourly space velocity of greater than or equal to 0.1 $h^{-1}$, greater than or equal to 0.5 $h^{-1}$, greater than or equal to 1 $h^{-1}$, greater than or equal to 5 $h^{-1}$, greater than or equal to 6 $h^{-1}$, greater than or equal to 10 $h^{-1}$, or even greater than or equal to 15 $h^{-1}$. The steam may be introduced to the steam enhanced catalytic crackers 114 at a gas hourly space velocity of less than or equal to 100 $h^{-1}$, less than or equal to 75 $h^{-1}$, less than or equal to 50 $h^{-1}$, less than or equal to 30 $h^{-1}$, or less than or equal to 20 h$^{-1}$. The steam may be introduced to the steam enhanced catalytic crackers 114 at a gas hourly space velocity of from 0.1 h$^{-1}$ to 100 h$^{-1}$, from 0.1 h$^{-1}$ to 75 h$^{-1}$, from 0.1 h$^{-1}$ to 50 h$^{-1}$, from 0.1 h$^{-1}$ to 30 h$^{-1}$, from 0.1 h$^{-1}$ to 20 h$^{-1}$, from 1 h$^{-1}$ to 100 h$^{-1}$, from 1 h$^{-1}$ to 75 h$^{-1}$, from 1 h$^{-1}$ to 50 h$^{-1}$, from 1 h$^{-1}$ to 30 h$^{-1}$, from 1 h$^{-1}$ to 20 h$^{-1}$, from 5 h$^{-1}$ to 100 h$^{-1}$, from 5 h$^{-1}$ to 75 h$^{-1}$, from 5 h$^{-1}$ to 50 h$^{-1}$, from 5 h$^{-1}$ to 30 h$^{-1}$, from 5 h$^{-1}$ to 20 h$^{-1}$, from 6 h$^{-1}$ to 100 h$^{-1}$, from 6 h$^{-1}$ to 75 h$^{-1}$, from 6 h$^{-1}$ to 50 h$^{-1}$, from 6 h$^{-1}$ to 30 h$^{-1}$, from 6 h$^{-1}$ to 20 h$^{-1}$, from 10 h$^{-1}$ to 100 h$^{-1}$, from 10 h$^{-1}$ to 75 h$^{-1}$, from 10 h$^{-1}$ to 50 h$^{-1}$, from 10 h$^{-1}$ to 30 h$^{-1}$, from 10 h$^{-1}$ to 20 h$^{-1}$, from 15 h$^{-1}$ to 100 h$^{-1}$, from 15 h$^{-1}$ to 75 h$^{-1}$, from 15 h$^{-1}$ to 50 h$^{-1}$, from 15 h$^{-1}$ to 30 h$^{-1}$, or from 15 h$^{-1}$ to 20 h$^{-1}$.

In embodiments, the feed (light $C_{5+}$ hydrocarbon stream 22 or heavy $C_{5+}$ hydrocarbon stream 24) may be injected into the steam enhanced catalytic crackers 114 at a gas hourly space velocity of greater than or equal to 0.1 per hour (h$^{-1}$) or greater than or equal to 0.25 h$^{-1}$. The feed may be injected into the steam enhanced catalytic crackers 114 at a gas hourly space velocity of less than or equal to 50 h$^{-1}$, less than or equal to 25 h$^{-1}$, less than or equal to 20 h$^{-1}$, less than or equal to 14 h$^{-1}$, less than or equal to 9 h$^{-1}$, or less than or equal to 5 h$^{-1}$. The feed may be injected into the steam enhanced catalytic crackers 114 at a gas hourly space velocity of from 0.1 h$^{-1}$ to 50 h$^{-1}$, from 0.1 h$^{-1}$ to 25 h$^-$, from 0.1 h$^{-1}$ to 20 h$^{-1}$, from 0.1 h$^{-1}$ to 14 h$^{-1}$, from 0.1 h$^{-1}$ to 9 h$^{-1}$, from 0.1 h$^{-1}$ to 5 h$^{-1}$, from 0.1 h$^{-1}$ to 4 h$^{-1}$, from 0.25 h$^{-1}$ to 50 h$^{-1}$, from 0.25 h$^{-1}$ to 25 h$^{-1}$, from 0.25 h$^{-1}$ to 20 h$^{-1}$, from 0.25 h$^{-1}$ to 14 h$^{-1}$, from 0.25 h$^{-1}$ to 9 h$^{-1}$, from 0.25 h$^{-1}$ to 5 h$^{-1}$, from 0.25 h$^{-1}$ to 4 v, from 1 h$^{-1}$ to 50 h$^{-1}$, from 1 h$^{-1}$ to 25 h$^{-1}$, from 1 h$^{-1}$ to 20 h$^{-1}$, from 1 h$^{-1}$ to 14 h$^{-1}$, from 1 h$^{-1}$ to 9 h$^{-1}$, or from 1 h$^{-1}$ to 5 h$^{-1}$.

In embodiments, the hourly space velocity may be different for the light steam enhanced catalytic cracker as compared to the heavy steam enhanced catalytic cracker. In one non-limiting example, the light $C_{5+}$ hydrocarbons stream 22 may require lesser hourly space velocities to give more time for the light $C_{5+}$ hydrocarbons stream 22 to be cracked into the desired products. In another non-limiting example, the heavy $C_{5+}$ hydrocarbons stream 24 may require greater hourly space velocities to prevent overcracking of the heavy $C_{5+}$ hydrocarbons stream 24 and prevent excess formation of petroleum coke. In embodiments, the hourly space velocity for the light steam enhanced catalytic cracker may be from 0.1 h$^{-1}$ to 1 h$^{-1}$. In embodiments, the hourly space velocity for the heavy steam enhanced catalytic cracker may be from 9 h$^{-1}$ to 40 h$^{-1}$.

In embodiments, the steam enhanced catalytic crackers 114 may operate at a temperature of from greater than or equal to 525° C., greater than or equal to 550° C., or greater than or equal to 575° C. The steam enhanced catalytic crackers 114 may be operated at a temperature of less than or equal to 750° C., less than or equal to 675° C., less than or equal to 650° C., or even less than or equal to 625° C. The steam enhanced catalytic crackers 114 may operate at temperatures of from 650° C. to 750° C. or from 675° C. to 750° C. The steam enhanced catalytic crackers 114 may be operated at temperatures of from 525° C. to 750° C., from 525° C. to 675° C., from 525° C. to 650° C., from 525° C. to 625° C., from 550° C. to 675° C., from 550° C. to 650° C., from 550° C. to 625° C., from 575° C. to 675° C., from 575° C. to 650° C., or from 575° C. to 625° C. The steam enhanced catalytic crackers 114 may be operated at a pressure of from 0.1 MPa to 0.2 MPa.

As previously discussed, the steam enhanced catalytic crackers 114 may produce olefins, and in particular, light olefins, such as ethylene, propylene, and butylene. In embodiments, the steam enhanced catalytic crackers may additionally produce gasoline as olefins. In embodiments, the ratio of olefins (gasoline) to light olefins produced may change depending on the operating temperatures used in the steam enhanced catalytic crackers 114. For example, operating temperatures between 500° C. to 650° C. may produce primarily propylene and gasoline over ethylene. As operating temperatures increase, the ratio moves further to producing primarily ethylene over propylene and gasoline. For example, operating temperatures between 650° C. to 680° C. may produce equal parts ethylene and propylene with less gasoline. At operating temperatures over 680° C., for example from 680° C. to 750° C., the reaction moves to primarily ethylene.

In embodiments, temperatures at the higher ends (>650° C.) of the operating range may be used to preferentially produce light olefins over heavier olefins, such as ethylene and propylene over gasoline. This may thereby make gasoline a by-product of the steam enhanced catalytic cracking reaction versus a primary product. Further temperature increases (>680° C.) may then minimize the amount of gasoline produced, primarily producing ethylene with propylene as a by-product. It is contemplated that the shifts discussed above may be related to reactions in the steam enhanced catalytic crackers moving from primarily catalytic cracking dominated at lower temperatures (500° C. to 650° C.) to primarily thermal cracking dominated at higher ends of the operating temperatures (>680° C.).

Still referring to FIG. 1, and in embodiments, the integrated system 100 may include the final product separator 116. The final product separator 116 may be fluidly connected to the first and second steam enhanced catalytic crackers 114 and may separate at least a portion of the light and heavy steam enhanced catalytically cracked products 26, 28, into at least one or more product streams and one or more recycle streams.

In embodiments, the one or more recycle streams may include a methane recycle stream 30, a steam cracker recycle stream 32, a hydrotreater recycle stream 34, a delayed coker recycle stream 36, or combinations thereof. The steam cracker recycle stream 32 may include $C_2$-$C_4$ hydrocarbons. The steam cracker recycle stream 32 may include $C_2$-$C_4$ paraffins, $C_2$-$C_4$ alkynes, or both. The steam cracker recycle stream 32 may include ethane, propane, butane, ethyne, propyne, butyne, or combinations thereof. The hydrotreater recycle stream 34 may include cracked naphtha, light cycle oil, heavy cycle oil, or combinations thereof. The delayed coker recycle stream 36 may include heavy cycle oil. In embodiments, the cracked naphtha may have boiling points of from an initial boiling point (IBP) of 25° C. to 204° C. The light cycle oil may have boiling points of between 343° C. to 426° C. The heavy cycle oil may have boiling points of greater than 426° C.

In embodiments, the one or more product streams may include a first product stream 38 and a second product stream 40. The first product stream 38 may include light olefins such as ethylene, propylene, butylene, or combinations thereof. The first product stream may also include olefins such as gasoline. The second product stream 40 may include aromatic compounds such as benzene, toluene, xylenes, or combinations thereof (also collectively referred to as "BTX"). The xylenes may include ortho-xylene, meta-xylene, and para-xylene. In embodiments, the first or second product streams may also include fuel oil (also known as heavy oil, marine fuel, or furnace oil), naphtha, off gas products ($C_1$-$C_4$ hydrocarbons), or combinations thereof.

The fuel oil and off-gas products may alternatively be included as part of the one or more recycle streams. In embodiments, the one or more product streams may include at least 45 wt. % $C_2$-$C_4$ olefins. The one or more products stream may include at least 30 wt. % naphtha. The one or more products stream may include at least 55 wt. % $C_2$-$C_4$ olefins. In embodiments, the one or more product streams may also include at least 20 wt. % naphtha. In embodiments, the one or more product streams may be combined into a single product stream.

In embodiments, the systems discussed herein may include additional components for the conversion of the hydrocarbon oil feedstocks. For example, the integrated system 100 may further include a methane cracker 110 fluidly connected to the hydrotreater 108 and final product separator 116. The methane cracker 110 may crack the $C_1$ hydrocarbon stream 14, the methane recycle stream 30, or both to produce hydrogen 16. The hydrogen 16 may be recycled and reused in the hydrotreater 108. In embodiments, the methane cracker may be operated at a temperature of from 850° C. to 1200° C. and at a pressure of from 1 bar to 2 bar. Without being bound by theory, hydrogen produced by methane cracking may also be incorporated in applications requiring pure hydrogen and no carbon monoxide (e.g., fuel cells).

As previously mentioned, and in embodiments, the hydrotreater 108 may include hydrogen 16. While the hydrogen 16 is discussed as coming from the methane cracker 110, it is also contemplated that the hydrogen 16 may come from additional sources, of which these additional sources may be the primary source for hydrogen used in the operation of the hydrotreater. In embodiments, the hydrotreater 108 may have a ratio of hydrogen 16 to feed (deasphalted oil stream 10 and delayed coker product stream 14) of from 800 L/L to 1200 L/L. The hydrotreater 108 may have a ratio of hydrogen 24 to feed of from 800 L/L to 1200 L/L, from 800 L/L to 1100 L/L, from 800 L/L to 1000 L/L, from 800 L/L to 900 L/L, from 900 L/L to 1200 L/L, from 900 L/L to 1100 L/L, from 900 L/L to 1000 L/L, from 1000 L/L to 1200 L/L, from 1000 L/L to 1100 L/L, from 1100 L/L to 1200 L/L, or from 1100 L/L to 1200 L/L.

In embodiments, the system 100 may further include a steam cracker 112. The steam cracker 112 may be fluidly connected to the hydrotreater 108 and final product separator 116 and may crack the $C_2$-$C_4$ hydrocarbon stream 18, the steam cracker recycle stream 32, or both, to form a steam cracked product stream 20. The steam cracked product stream 20 may include a mixture of cracked hydrocarbon-based materials, which may be separated into one or more petrochemical products that are included in the first or second product streams. For example, the steam cracked product stream may include $C_2$-$C_4$ olefins, benzene, toluene, xylene, naphtha, or combinations thereof, and optionally, fuel gas, butadiene, $C_{5+}$ hydrocarbons, fuel oil, or combinations thereof. In embodiments, the steam cracker 112 may operate at a temperature of from 700° C. to 950° C., such as from 800° C. to 950° C., or from 900° C. to 950° C. and at a pressure of from 0.1 MPa to 0.2 MPa. The steam cracker may operate with a residence time of from 0.05 seconds to 2 seconds. The mass ratio of steam to the $C_2$-$C_4$ hydrocarbon fraction 106 may be from about 0.3:1 to about 2:1.

In embodiments, the hydrotreater 108 may additionally be fluidly connected to the final product separator 116 and may hydrotreat the hydrotreater recycle stream 34 to produce additional hydrotreater product stream. The delayed coker 106 may additionally be fluidly connected to the final product separator 116 and may de-coke the delayed coker recycle stream 36 to form additional petroleum coke 42 and delayed coker product stream 12. In embodiments, the final product separator 116 may send the methane recycle stream 30 to the methane cracker 110, the steam cracker recycle stream 32 to the steam cracker 112, the hydrotreater recycle stream 34 to the hydrotreater 108, the delayed coker recycle stream 36 to the delayed coker 106, or combinations thereof.

Figure 3:
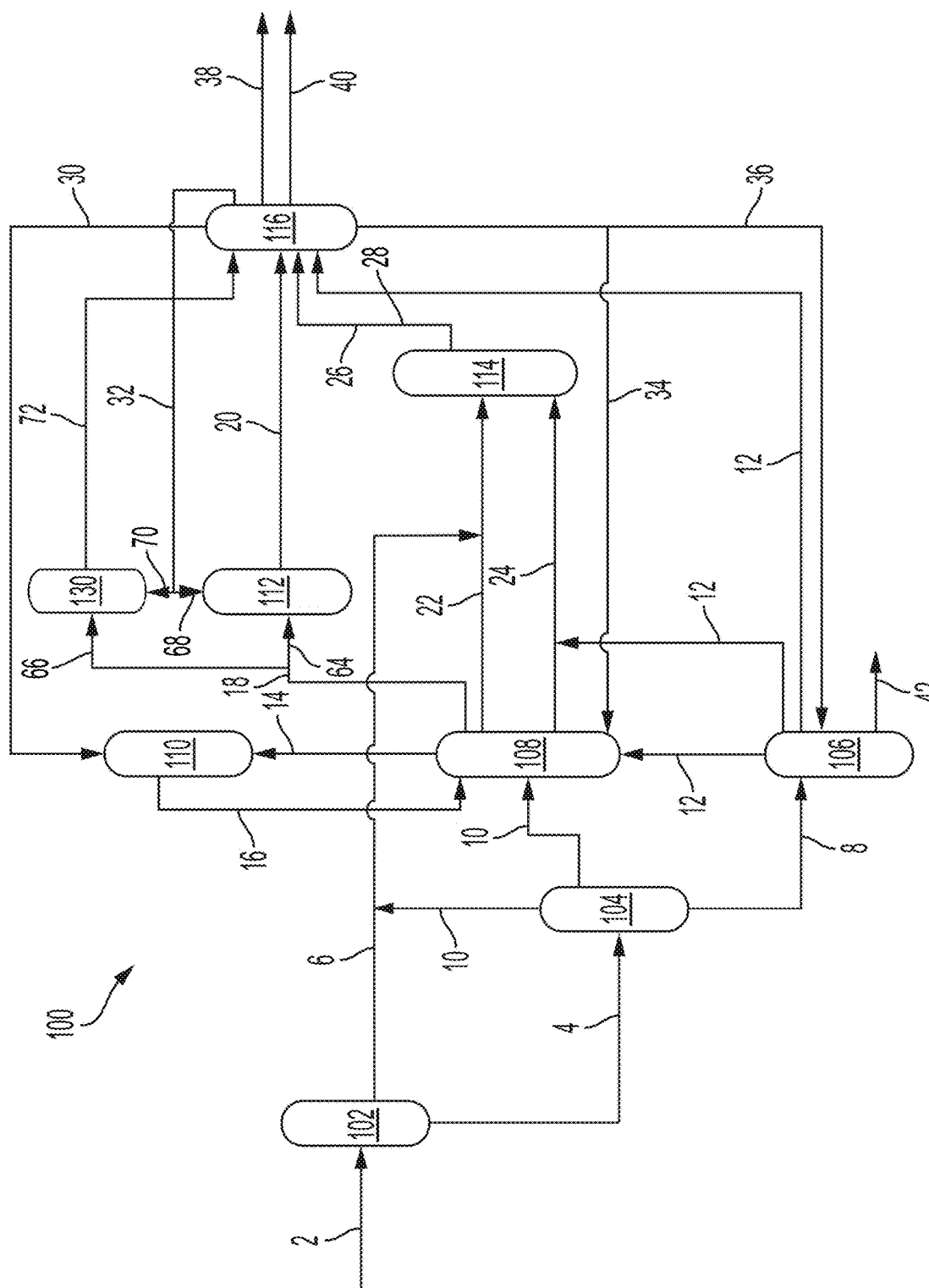
FIG. 3 illustrates a process flow diagram for an exemplary process in accordance with embodiments described herein.
Figure 4:
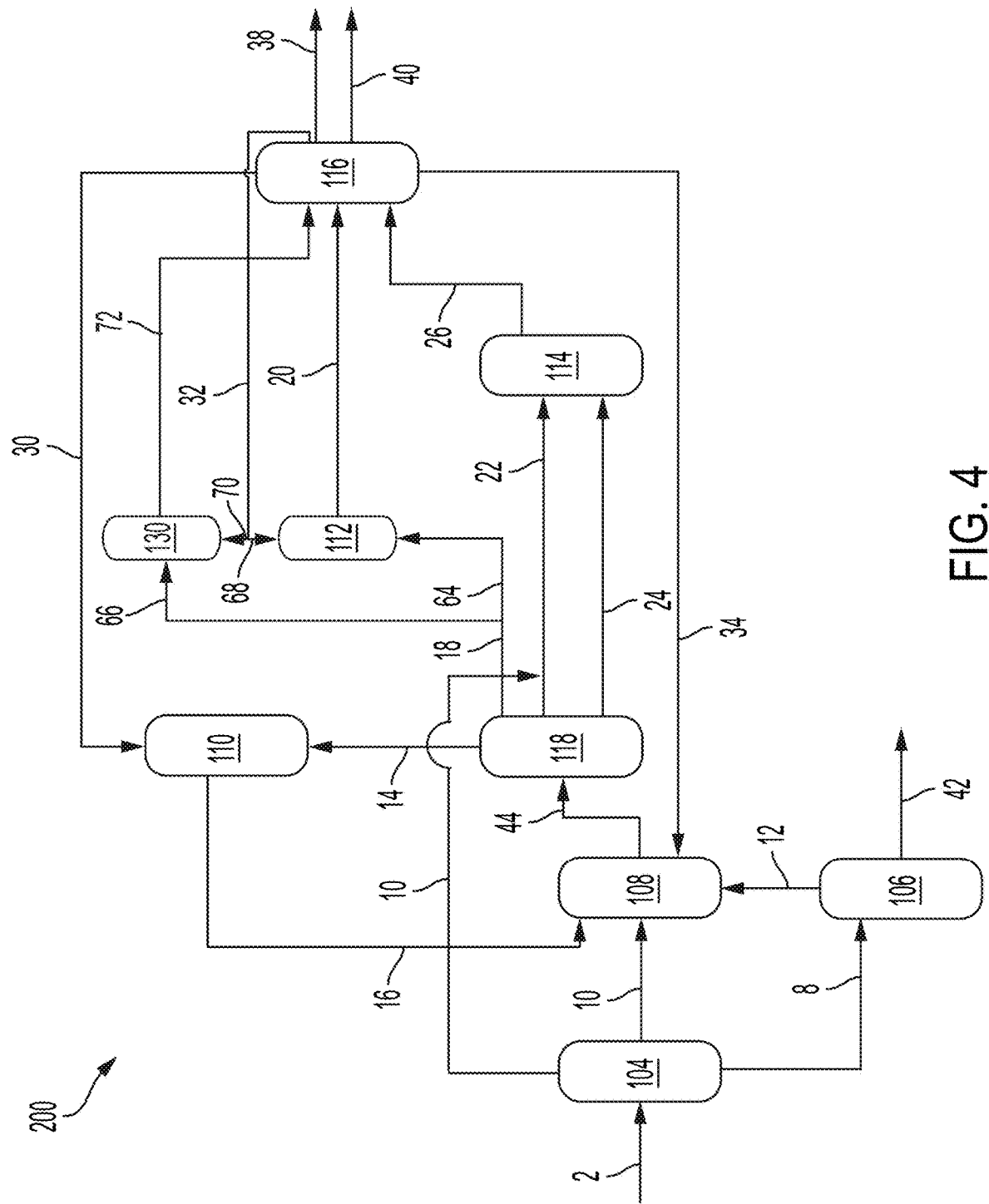
FIG. 4 illustrates a process flow diagram for an exemplary process in accordance with embodiments described herein.

Now referring to FIGS. 3 and 4, and in embodiments, the integrated system 100 may also include a dehydrogenation unit 130. The dehydrogenation unit 130 may be fluidly connected to the hydrotreater 108 and the final product separator 116. The dehydrogenation unit 130 may dehydrogenate a $C_3$-$C_4$ portion 66 of the $C_2$-$C_4$ hydrocarbon stream 18, a $C_3$-$C_4$ portion (also referred to herein as a $C_3$-$C_4$ hydrocarbon recycle stream 70) of the steam cracker recycle stream 33, or both to form the propylene and butylene 72. In this configuration, the hydrotreater 108 may be additionally configured to produce a $C_3$-$C_4$ hydrocarbon stream 66, a $C_2$ hydrocarbon stream 64, or both. The dehydrogenation unit 130 may then send the propylene and butylene 72 to the final product separator 116, where the propylene and butylene 72 may be separated in the one or more product streams. In these embodiments, the steam cracker 112 may crack a $C_2$ portion 64 of the $C_2$-$C_4$ hydrocarbon stream 18, a $C_2$ portion (also referred to herein as a $C_2$ hydrocarbon recycle stream 68) of the steam cracker recycle stream 32, or both to form light olefins, naphtha, and BTX.

In embodiments, the dehydrogenation unit 130 may operate at a temperature of from 300° C. to 800° C., such as from 300° C. to 400° C., from 400° C. to 500° C., from 500° C. to 600° C., from 600° C. to 700° C., from 700° C. to 800° C., or any combinations thereof. The dehydrogenation unit 130 may also operate at a pressure of from 0.001 MPa to 1 MPa. Without being bound by any particular theory, it is believed that since the dehydrogenation of hydrocarbons is an endothermic reaction and conversion levels are limited by chemical equilibrium, it may be desirable to operate at relatively high temperatures and relatively low hydrogen partial pressures in order to achieve greater conversion. However, for reactions under severe conditions it may be difficult to maintain high activity and selectivity for long periods of time because undesirable side reactions such as aromatization, cracking, isomerization, coke formation, or combinations thereof, may increase. Therefore, reaction conditions may be selected with regard to maximizing one or more of catalytic activity, catalytic selectivity, and catalyst stability.

In embodiments, the dehydrogenation unit 130 may also include a catalyst system for conversion of hydrocarbons. The catalyst system may include a zincosilicate support material, one or more alkali or alkaline earth metals, and one or more platinum group metals. The zincosilicate support material may further include a MFI framework type structure incorporating at least silicon and zinc. As used herein, a "MFI framework type structure" may sometimes be referred to as a ZSM-5 framework type structure. Zeolitic framework types, such as the MFI framework type, are disclosed in "Atlas of Zeolite Framework Types, Fifth Edition" by Baerlcher, Meier, and Olson, the contents of which are incorporated by reference in their entirety. Dehydrogenating $C_3$-$C_4$ hydrocarbons may further include contacting the $C_3$-$C_4$ hydrocarbons with the catalyst system to dehydrogenate at least a portion of the $C_3$-$C_4$ hydrocarbons into the propylene and butylene.

In embodiments, the system 100 may further include a feed separator 102. The feed separator 102 may be a series of vapor-liquid separators such as flash tanks or flash drums (also referred to as a breakpot, knock-out drum, knock-out pot, compressor suction drum, or compressor inlet drum). It should be understood that a wide variety of fractionating separators may be utilized, such as distillation columns and the like. The feed separator 102 may be fluidly connected to the solvent deasphalting unit 104 and the steam enhanced catalytic crackers 114. The feed separator 102 may initially separate the hydrocarbon oil stream 2 into a light oil fraction stream 6 and a heavy oil fraction stream 4. The feed separator 102 may then send the light oil fraction stream 6 to the steam enhanced catalytic crackers 114. In these embodiments, the solvent deasphalting unit 104 may separate the heavy oil fraction stream 4 into at least the heavy residual hydrocarbons 8 and the de-asphalted oil stream 10. Also, in these embodiments, the first steam enhanced catalytic cracker may crack the light oil fraction stream 6 into the light steam enhanced catalytically cracked product 26.

Figure 2:
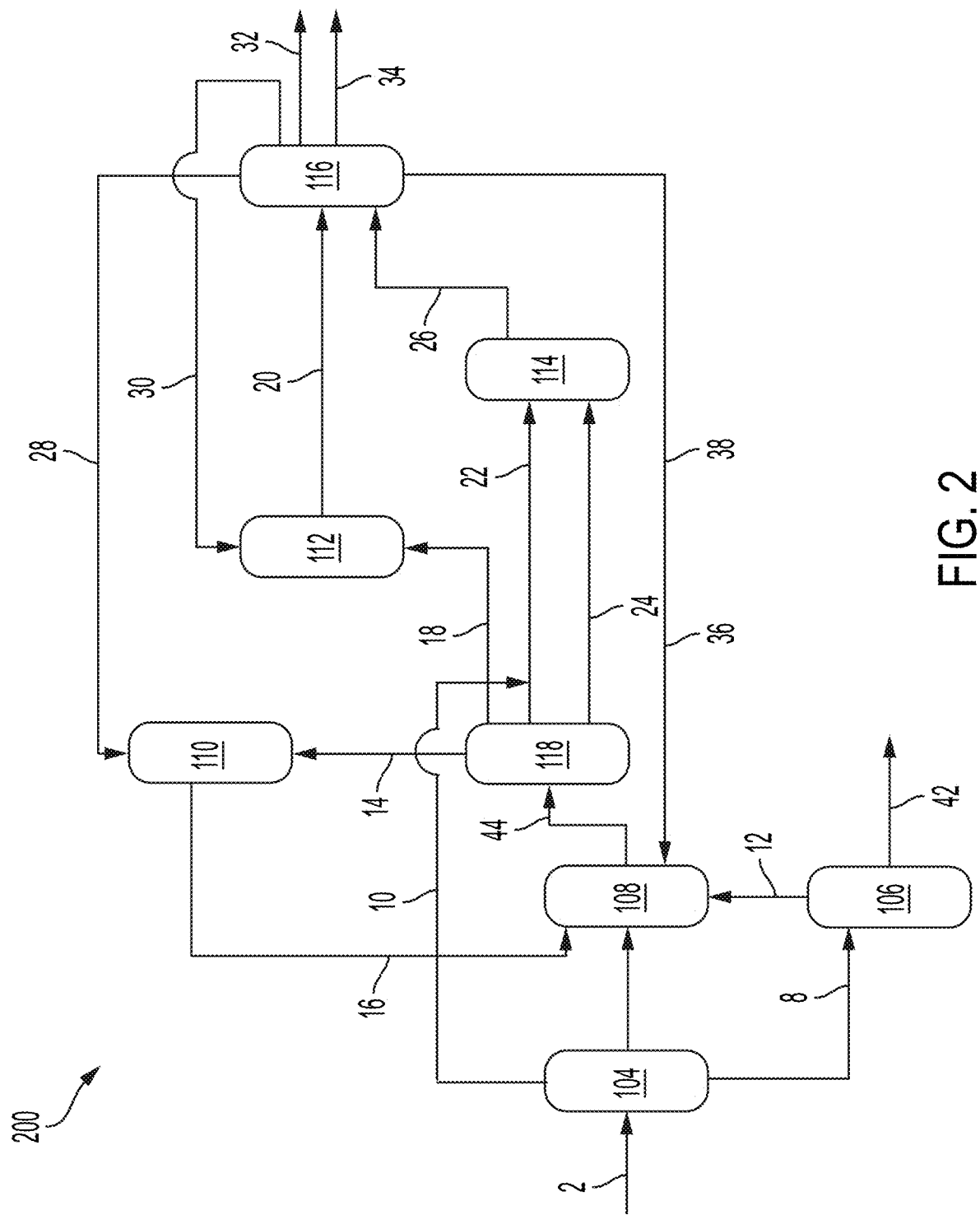
FIG. 2 illustrates a process flow diagram for an exemplary process in accordance with embodiments described herein.

Now referring to FIG. 2, an integrated system 200 for the conversion of hydrocarbon oil feedstocks is illustrated. The integrated system 200 may include any of the integrated systems 100 previously or hereinafter discussed as well as additional components. The integrated system 200 may also include any of the hydrocarbon oil streams 2 previously or hereinafter discussed. In embodiments, the integrated system 200 may further include a first product separator 118. As illustrated in FIG. 2, the first product separator 118 may be fluidly connected to the hydrotreater 108, the methane cracker 110, the steam cracker 112, the first steam enhanced catalytic cracker, and the second steam enhanced catalytic cracker. The first product separator 118 may separate the hydrotreated product stream into the $C_1$ hydrocarbon stream 14, the $C_2$-$C_4$ hydrocarbon stream 18, the light $C_{5+}$ hydrocarbon stream 22, and the heavy $C_{5+}$ hydrocarbon stream 24. The first product separator 118 may also send the $C_1$ hydrocarbon stream 14 to the methane cracker 110, the $C_2$-$C_4$ hydrocarbon stream 18 to the steam cracker 112, the light $C_{5+}$ hydrocarbon stream 22 to the first steam enhanced catalytic cracker, and the heavy $C_{5+}$ hydrocarbon stream 24 to the second steam enhanced catalytic cracker.

In embodiments, the systems 100 and 200 may further include a hydrocracker. The hydrocracker may be used in place of the hydrotreater 108 to upgrade the delayed coker product stream, the deasphalted oil stream, or both to produce hydrocracker product streams in place of the hydrotreater product streams. In embodiments with the hydrocracker in place of the hydrotreater 108, the hydrocracker may provide the additional advantage of cracking the heaviest hydrocarbon components of the delayed coker product stream 14, the deasphalted oil stream 10, or both to form olefins, BTX, and naphtha, similar to the function of the second steam enhanced catalytic cracker.

In other embodiments, the hydrocracker may be included in addition to the hydrotreater 108. In these embodiments, the hydrocracker may be downstream of and fluidly connected to the hydrotreater 108. The hydrocracker may also be fluidly connected to the final product separator 116. The hydrotreater 108 may be additionally configured to send at least a portion of the heavy $C_{5+}$ hydrocarbon stream 24 to the hydrocracker as a heaviest $C_{5+}$ hydrocarbon stream. The heaviest $C_{5+}$ hydrocarbon stream may include $C_{5+}$ hydrocarbons having boiling points of from 540° C. to 640° C. In embodiments, the heaviest $C_{5+}$ hydrocarbon stream may also generally include the hydrocarbon residues having an API gravity of at least 8.0° and/or a standard liquid density of at least 1,000 kilograms per cubic meter ($kg/m^3$), as previously mentioned. The hydrocracker may crack the heaviest $C_{5+}$ hydrocarbon stream to form olefins, BTX, and naphtha. The hydrocracker may also be additionally configured to send the olefins, BTX, and naphtha to the product separator 116.

Still referring to FIGS. 1 and 2, embodiments of the present disclosure also include integrated processes for upgrading a hydrocarbon oil feed stream. The processes may include any of the integrated systems 100 and 200 previously described. The process includes solvent deasphalting the hydrocarbon oil stream 2 to form at least the deasphalted oil stream 10 and the heavy residual hydrocarbons 8. The process further includes delayed coking the heavy residual hydrocarbons 8 to form the petroleum coke 12 and the delayed coker product stream 14. The process further includes hydrotreating the delayed coker product stream 14 and the deasphalted oil stream 10 to form the light $C_{5+}$ hydrocarbon stream 22 and the heavy $C_{5+}$ hydrocarbon stream 24. The process further includes steam enhanced catalytically cracking the light $C_{5+}$ hydrocarbon stream 22 to form the light steam enhanced catalytically cracked product stream 26. The process further includes steam enhanced catalytically cracking the heavy $C_{5+}$ hydrocarbon stream 24 to form the heavy steam enhanced catalytically cracked product stream 28.

In embodiments, the process may further include passing at least a portion of the light steam enhanced catalytically cracked stream 26, the heavy steam enhanced catalytically cracked product stream 28, or both to the final product separator 116 to produce the one or more product streams and the one or more recycle streams. In embodiments, the process may further include hydrotreating the delayed coker product stream 14 and the deasphalted oil stream 10 to additionally form the $C_1$ hydrocarbon stream 14 and the $C_2$-$C_4$ hydrocarbon stream 18.

In embodiments, the process may further include delayed coking the delayed coker recycle stream 36 to form additional delayed coker product stream 14, hydrotreating the hydrotreater recycle stream 34 to form additional hydrotreated product stream, methane cracking the $C_1$ hydrocarbon stream 14, the methane recycle stream 30, or both to form hydrogen 16, steam cracking the $C_2$-$C_4$ hydrocarbon stream 18, the steam cracker recycle stream 32, or both to form the steam cracked product stream 20. The process may also further include passing the hydrogen 16 to the hydrotreater 108 to be recycled in the hydrotreater 108 and passing the steam cracked product stream 20 to the final separator 116 to produce the one or more product streams and the one or more recycle streams.

In embodiments including the dehydrogenation unit, the process may further include steam cracking a $C_2$ portion of the $C_2$-$C_4$ hydrocarbon stream 18, a $C_2$ portion of the steam cracker recycle stream 32, or both, to form light olefins, naphtha, and BTX. The process may also further include dehydrogenating a $C_3$-$C_4$ portion of the $C_2$-$C_4$ hydrocarbon stream 18, a $C_3$-$C_4$ portion of the steam cracker recycle stream 32, or both to form propylene and butylene. The process may also further yet include passing the propylene and butylene to the final separator 116 to produce the one or more product streams.

In embodiments including the first product separator 118, the process may further include passing the hydrotreated product stream to the first product separator 118 to separate the $C_1$ hydrocarbon stream 14, the $C_2$-$C_4$ hydrocarbon stream 18, the light $C_{5+}$ hydrocarbon stream 22, the heavy $C_{5+}$ hydrocarbon stream 24, or combinations thereof.

In embodiments including the feed separator 102, the process may further include initially passing the hydrocarbon oil stream 2 through the feed separator 102 to separate the hydrocarbon oil stream 2 into the heavy hydrocarbon fraction 4 and the light hydrocarbon fraction 6. The process may also further include solvent deasphalting the heavy hydrocarbon fraction 4 to form at least the deasphalted oil stream 10 and the heavy residual hydrocarbons 8. The process may also further yet include steam enhanced catalytically cracking at least the light hydrocarbon fraction 6 in the first steam enhanced catalytic cracker to form the light steam enhanced catalytically cracked product 26.

EXAMPLES

The various embodiments of methods and systems for the conversion of a hydrocarbon oil will be further clarified by the following examples. The examples are illustrative in nature, and should not be understood to limit the subject matter of the present disclosure.

Example 1

Arab light crude oil (AL), Arab extra light crude oil (AXL), and Arab heavy crude oil (AH) were processed in a simulation program using the systems illustrated in FIGS. 1 and 2. The compositions of crude oil used in the Examples are shown below in Tables 2 and 3.

TABLE 2

Arab Extra Light, Arab Light, and Arab Heavy Crude Oil Compositions

| Feed | AXL | AL | AH |
|---|---|---|---|
| Density at 15.6° C. | 0.8412 | 0.8658 | 0.8871 |
| Percentage $C_1$-$C_4$ hydrocarbon fractions | 5.49 | 4.46 | 3.25 |
| Percentage <300° C. boiling point hydrocarbon fractions | 49.59 | 39.85 | 30.65 |
| Percentage >300° C. boiling point hydrocarbon fractions | 44.92 | 55.69 | 66.0 |

TABLE 3

Arab Extra Light, Arab Light, and Arab Heavy Crude Oil Compositions

| Feed | AXL | AL | AH |
|---|---|---|---|
| Light Fraction (<300° C. boiling point) | | | |
| Percentage C1-C5 hydrocarbons | 5.49 | 4.46 | 3.25 |
| Liquefied Natural Gas (C5 hydrocarbons to <300° C. boiling point fractions) | 49.59 | 39.85 | 30.65 |
| Heavy Fraction (>300° C. boiling point) | | | |
| 300° C. to 385° C. boiling point hydrocarbon fractions (diesel products) | 15.01 | 13.96 | 13.24 |
| 385° C. to 540° C. boiling point hydrocarbon fractions (vacuum gas oil) | 18.59 | 20.18 | 19.3 |
| >540° C. boiling point hydrocarbon fractions (vacuum residuals) | 11.32 | 21.55 | 33.56 |

Table 4 below illustrates the simulation results using Arab extra light crude oil and Arab heavy crude oil as the feedstocks. The simulation was performed according to the configuration illustrated in FIG. 1 for Inventive Example 1 and FIG. 2 for Example 2. Similarly, Comparative Examples 1 were performed according to FIG. 1, but without the solvent deasphalting unit or the delayed coker. Comparative Example 2 was performed according to FIG. 2, but without the delayed coker.

The simulation was performed according to the configuration illustrated in FIG. 3 for Inventive Example 3. Comparative Example 3 was performed according to FIG. 3, but without the dehydrogenating unit. Comparative Example 4 was also performed according to FIG. 3, but without the delayed coker or deasphalting unit. Inventive Examples 1 and 3 and Comparative Examples 1, 3, and 4 used Arab extra light crude oil. Inventive Example 2 and Comparative Example 2 used Arab heavy crude oil.

TABLE 4

Inventive Example Testing Overall Yield

| Component | Inventive Example 1 | Inventive Example 2 | Inventive Example 3 | Comparative Example 1 | Comparative Example 2 | Comparative Example 3 | Comparative Example 4 |
|---|---|---|---|---|---|---|---|
| | | | | Weight Percentage Component | | | |
| Hydrogen | 3.1 | 1.8 | 2.9 | 3.1 | 1.3 | 2.9 | 2.9 |
| Petroleum Coke | 7.6 | 8.2 | 7.1 | 6.7 | 2.9 | 7.1 | 7.1 |
| Ethylene | 22.8 | 11.5 | 23.0 | 23.7 | 9.7 | 23.0 | 23.8 |
| Propylene | 23.1 | 23.8 | 26.2 | 24.3 | 20.9 | 24.2 | 27.5 |
| Butylene | 13.2 | 13.2 | 15.9 | 13.7 | 11.7 | 14.0 | 16.4 |
| BTX | 0.3 | 0.3 | 0.1 | 0.3 | 0.3 | 0.1 | 0.1 |
| Naphtha | 21.6 | 30.6 | 20.6 | 19.1 | 27.8 | 20.6 | 18.8 |
| Purge and Other products | 8.3 | 10.6 | 4.2 | 8.992 | 25.3 | 8.2 | 3.6 |

In Table 4 above, the "Purge and Other Products" may include crude oil fractions not previously mentioned in the preceding components. The Purge and Other Products may also include waste or unusable streams. For example, the Purge and Other Products may include light cycle oils, heavy cycle oils, distillate, and $C_1$, and $C_2$-$C_4$ paraffins. The heavy cycle oil may be used, for example, as fuel oil for boilers.

In Table 4 above, it is contemplated that the greater amount of olefins present in Comparative Example 1 as compared to Inventive Example 1 is due to the exclusion of the delayed coker and deasphalting unit. Because the deasphalting unit and delayed coker are excluded in comparative example 1, the heavy streams ordinarily processed in the delayed coker and deasphalting unit are instead sent to the steam enhanced catalytic crackers. This increases the throughput in the steam enhanced catalytic crackers and thus the olefin yield. However, this configuration also results in a lesser amount of naphtha within the product streams, which may in turn reduce the yields of BTX if the naphtha is later processed and upgraded to aromatics such as benzene, toluene, and xylenes. However, this phenomenon may also be dependent on the crude oil feed that is chosen. For example, Inventive Example 2 and Comparative Example 2 processed Arab heavy crude oil. The Arab heavy crude oil, with its greater amounts of heavier (greater boiling point) hydrocarbon components, showed a marked reduction in generation of both olefins and naphtha when the solvent deasphalting unit and delayed coker were not included. This may illustrate the particular suitability of the systems discussed herein towards processing and upgrading of heavier grades of crude oil.

Table 5 below illustrates the simulation results using Inventive Example 1 as the feedstock. The simulation was performed according to the configuration illustrated in FIG. 1, but without recycle streams from the final product separator.

TABLE 5

Inventive Example 1 Product Yields by Processing Unit

| Delayed Coker | | Hydrotreater | | Steam Cracker | | SECC for Light Fraction | | SECC for Heavy Fraction | |
| --- | --- | --- | --- | --- | --- | --- | --- | --- | --- |
| Product | wt. % | Product | wt. % | Product | wt. % | Product | wt. % | Product | wt. % |
| Methane and Non-hydrocarbon constituents | 10.9 | Methane and Hydrogen | 1.8 | Methane and Hydrogen | 21.08 | Methane | 11.2 | Methane and Hydrogen | 3.2 |
| $C_3$ to $C_4$ Hydrocarbons | 6.1 | Liquefied Petroleum Gas ($C_2$ to $C_4$) | 0.1 | Ethylene | 51.87 | C2-C4 Paraffins | 5.9 | C2-C4 Paraffins | 8.2 |
| Coker Naphtha Stream (C5-180° C. boiling point) | 18.4 | Naphtha (185° C. to 204° C.) | 25.1 | Propylene | 11.92 | C2-C4 Olefins | 62.9 | C2-C4 Olefins | 36.4 |
| Coker Gas Oil Stream (180° C. to 340° C.) | 25.1 | Distillate (204° C. to 343° C.) | 47.2 | Butadiene | 2.8 | Naphtha & Gasoline | 11.2 | Naphtha & Gasoline | 32.4 |
| Coker Heavy Cycle Oil Stream (>340° C.) | 39.4 | Gas Oil | 25.8 | BTX | 2.56 | Light Cycle Oil | 6.3 | Light Cycle Oil | 6.7 |
| | | Heavy Cycle Oil & Atmospheric Residue Oil (>340° C.) | 0.1 | C5+ Hydrocarbons | 8.92 | Heavy Cycle Oil | 0.3 | Heavy Cycle Oil | 4.7 |
| | | | | Fuel Oil | 0.85 | Coke | 2.3 | Coke | 8.2 |

Referring to Table 5, all of the delayed coker products were sent to the hydrotreater with exception to the petroleum coke. In regards to the hydrotreater, the methane and hydrogen were sent to a methane cracker for production of primarily hydrogen. The liquefied petroleum gas was sent to the steam cracker for conversion to the steam cracker products. The naphtha from the hydrotreater was sent to the first steam enhanced catalytic cracker, for conversion to the first steam enhanced catalytic cracker products. The distillate, gas oil, heavy cycle oil, and atmospheric residue oil were sent to the second steam enhanced catalytic cracker, for conversion to the second steam enhanced catalytic cracker products. The distillate was primarily composed of diesel and kerosene boiling point hydrocarbon fractions. All of the steam cracker products were sent to the product separator. All of the products from both of the steam enhanced catalytic crackers were also sent to the product separator.

Table 6 below illustrates the simulation results for Comparative Example 1. The simulation was performed similar to that for Inventive Example 1, but without the delayed coker or deasphalting unit.

TABLE 6

Comparative Example 1 Product Yields by Processing Unit

| Hydrotreater | | Steam Cracker | | SECC for Light Fraction | | SECC for Heavy Fraction | |
| --- | --- | --- | --- | --- | --- | --- | --- |
| Product | wt. % | Product | wt. % | Product | wt. % | Product | wt. % |
| Methane and Hydrogen | 1.8 | Methane and Hydrogen | 21.12 | Methane | 11.4 | Methane and Hydrogen | 3.6 |
| Liquefied Petroleum Gas ($C_2$ to $C_4$) | 0.1 | Ethylene | 51.88 | Non-Olefin $C_2$-$C_4$ Hydrocarbons | 6.0 | $C_2$-$C_4$ Paraffins | 8.5 |
| Naphtha (185° C. to 204° C.) | 23.8 | Propylene | 11.92 | Light Olefins | 64.4 | $C_2$-$C_4$ Olefins | 37.5 |
| Distillate (204° C. to 343° C.) | 48.3 | Butadiene | 2.79 | Naphtha & Gasoline | 9.7 | Naphtha & Gasoline | 28.5 |
| Gas Oil | 26.1 | BTX | 2.55 | Light Cycle Oil | 6.0 | Light Cycle Oil | 7.4 |
| Heavy Cycle Oil & Atmospheric Residue Oil (>340° C.) | 0.0 | C5+ Hydrocarbons | 8.88 | Heavy Cycle Oil | 0.3 | Heavy Cycle Oil | 7.4 |
| | | Fuel Oil | 0.0 | Coke | 2.3 | Coke | 7.1 |

As illustrated in Tables 4, 5, and 6 above, including the delayed coker while processing the Arab Extra Light Crude Oil resulted in a higher concentration of products in the naphtha boiling point range for each of the processing units, as well as in the final product stream. For example, inclusion of the delayed coking unit resulted in an increase of naphtha in the hydrotreater product stream and the final product stream of 1.3 wt. % and 2.5 wt. %, respectively. It is contemplated that the higher percentage of naphtha may also result in a higher percentage of BTX for the product streams if the naphtha is processed in, for example, an aromatization unit. As shown in Tables 7 and 8 below, this higher concentration of products in the naphtha boiling range effect is further exaggerated as the crude oil stream includes greater amounts of the heavy fraction (>300° C. boiling point hydrocarbons).

Table 7 below illustrates the simulation results using Arab heavy crude oil as the feedstock. The simulation was performed according to the configuration illustrated in FIG. 2, but without recycle streams from the final product separator. The products of each of the treatment units of Table 5 below were distributed to the other units in a similar manner as for Table 4 above.

TABLE 7

Inventive Example 2 Product Yields by Processing Unit

| Delayed Coker | | Hydrotreater | | Steam Cracker | | SECC | |
| --- | --- | --- | --- | --- | --- | --- | --- |
| Product | wt. % | Product | wt. % | Product | wt. % | Product | wt. % |
| Methane and Non-hydrocarbon constituents | 11.6 | Methane and Hydrogen | 1.8 | Methane and Hydrogen | 22.96 | Methane | 3.4 |
| $C_3$ to $C_4$ Hydrocarbons | 6.1 | Liquefied Petroleum Gas ($C_2$ to $C_4$) | 0.9 | Ethylene | 47.86 | Non-Olefin $C_2$-$C_4$ Hydrocarbons | 8.8 |

TABLE 7-continued

Inventive Example 2 Product Yields by Processing Unit

| Delayed Coker | | Hydrotreater | | Steam Cracker | | SECC | |
|---|---|---|---|---|---|---|---|
| Product | wt. % | Product | wt. % | Product | wt. % | Product | wt. % |
| Coker Naphtha Stream (C5-180° C. boiling point) | 18.6 | Naphtha (185° C. to 204° C.) | 20.0 | Propylene | 13.47 | Light Olefins | 39.1 |
| Coker Gas Oil Stream (180° C. to 340° C.) | 25 | Distillate (204° C. to 343° C.) | 30.4 | Butadiene | 2.76 | Naphtha & Gasoline | 25.8 |
| Coker Heavy Cycle Oil Stream (>340° C.) | 38.6 | Gas Oil | 39.3 | BTX | 2.44 | Light Cycle Oil | 7.2 |
| | | Heavy Cycle Oil & Atmospheric Residue Oil (>340° C.) | 7.5 | C5+ Hydrocarbons | 9.58 | Heavy Cycle Oil | 5.9 |
| | | | | Fuel Oil | 0.93 | Coke | 9.9 |

Table 8 below illustrates the simulation results for Comparative Example 2. The simulation was performed similar to that for Inventive Example but without the delayed coker.

TABLE 8

Comparative Example 2 Product Yields by Processing Unit

| Delayed Coker | | Hydrotreater | | Steam Cracker | | SECC | |
|---|---|---|---|---|---|---|---|
| Product | wt. % | Product | wt. % | Product | wt. % | Product | wt. % |
| Methane and Non-hydrocarbon constituents | 11.6 | Methane and Hydrogen | 2.0 | Methane and Hydrogen | 23.20 | Methane | 3.4 |
| $C_3$ to $C_4$ Hydrocarbons | 6.1 | Liquefied Petroleum Gas ($C_2$ to $C_4$) | 1.3 | Ethylene | 46.65 | Non-Olefin C2-C4 Hydrocarbons | 8.6 |
| Coker Naphtha Stream (C5-180° C. boiling point) | 18.6 | Naphtha (185° C. to 204° C.) | 26.7 | Propylene | 13.90 | Light Olefins | 38.2 |
| Coker Gas Oil Stream (180° C. to 340° C.) | 25 | Distillate (204° C. to 343° C.) | 32.8 | Butadiene | 2.79 | Naphtha & Gasoline | 27.6 |
| Coker Heavy Cycle Oil Stream (>340° C.) | 38.6 | Gas Oil | 27.1 | BTX | 0.00 | Light Cycle Oil | 6.8 |
| | | Heavy Cycle Oil & Atmospheric Residue Oil (>340° C.) | 10.1 | C5+ Hydrocarbons | 9.99 | Heavy Cycle Oil | 4.0 |
| | | | | Fuel Oil | 2.23 | Coke | 11.3 |

As illustrated in Tables 7 and 8 above, including the delayed coker while processing the Arab Heavy Crude Oil resulted in a higher concentration of products in the naphtha boiling point range for each of the processing units, as well as in the final product stream. For example, inclusion of the delayed coking unit resulted in an increase of naphtha in the hydrotreater product stream and the final product stream of 6.7 wt. % and 2.8 wt. %, respectively. Further, inclusion of the delayed coker unit also resulted in higher concentrations of light olefins, such as ethylene, propylene, and butylene. As previously stated, the concentration of products in the naphtha range was further exaggerated when using a heavier crude oil. It is contemplated that the higher percentage of naphtha may also result in a higher percentage of BTX for the product streams if the naphtha is processed in, for example, an aromatization unit.

Table 9 below illustrates the simulation results using Inventive Example 3 as the feedstock. The simulation was performed according to the configuration illustrated in FIG. 3, but without recycle streams from the final product separator. Although not listed in Table 9 below, $C_3$ and $C_4$ hydrocarbons entering the dehydrogenation unit had approximately a 100% conversion rate to propylene and butylene, respectively.

TABLE 9

Inventive Example 3 Product Yields by Processing Unit

| Delayed Coker | | Hydrotreater | | Steam Cracker | | SECC for Light Fraction | | SECC for Heavy Fraction | |
| --- | --- | --- | --- | --- | --- | --- | --- | --- | --- |
| Product | wt. % | Product | wt. % | Product | wt. % | Product | wt. % | Product | wt. % |
| Methane and Non-hydrocarbon constituents | 10.9 | Methane and Hydrogen | 1.7 | Methane and Hydrogen | 17.03 | Methane | 11.6 | Methane and Hydrogen | 3.2 |
| $C_3$ to $C_4$ Hydrocarbons | 6.1 | Liquefied Petroleum Gas ($C_2$ to $C_4$) | 0.0 | Ethylene | 66.97 | C2-C4 Paraffins | 6.1 | C2-C4 Paraffins | 8.2 |
| Coker Naphtha Stream (C5-180° C. boiling point) | 18.4 | Naphtha (185° C. to 204° C.) | 22.3 | Propylene | 6.75 | C2-C4 Olefins | 66.1 | C2-C4 Olefins | 36.7 |
| Coker Gas Oil Stream (180° C. to 340° C.) | 25.1 | Distillate (204° C. to 343° C.) | 45.8 | Butadiene | 2.35 | Naphtha & Gasoline | 8.1 | Naphtha & Gasoline | 30.6 |
| Coker Heavy Cycle Oil Stream (>340° C.) | 39.4 | Gas Oil | 30.2 | BTX | 0.00 | Light Cycle Oil | 5.6 | Light Cycle Oil | 7.9 |
| | | Heavy Cycle Oil & Atmospheric Residue Oil (>340° C.) | 0.0 | C5+ Hydrocarbons | 5.01 | Heavy Cycle Oil | 0.2 | Heavy Cycle Oil | 6.8 |
| | | Fuel Oil | 1.26 | Coke | 2.3 | Coke | 6.5 | | |

As illustrated by Inventive Example 3 and Comparative Example 3 in Table 4 above, including the dehydrogenation unit resulted in a higher concentrations of olefins in the final product stream while not affecting the yield of Naphtha range products. For example, inclusion of the dehydrogenation unit resulted in an increase in olefin yield in the final product stream of approximately 3.9 wt. % comparing Inventive Example 3 and Comparative Example 3.

The present application discloses several technical aspects. One aspect is an integrated process for upgrading a hydrocarbon oil feed stream utilizing a delayed coker and steam enhanced catalytic cracker, the method including: solvent deasphalting the hydrocarbon oil stream to form at least a deasphalted oil stream and heavy residual hydrocarbons, the heavy residual hydrocarbons including at least asphaltenes; delayed coking the heavy residual hydrocarbons to form petroleum coke and a delayed coker product stream; hydrotreating the delayed coker product stream and the deasphalted oil stream to form a light $C_{5+}$ hydrocarbon stream, and a heavy $C_{5+}$ hydrocarbon stream; steam enhanced catalytically cracking the light $C_{5+}$ hydrocarbon stream to form a light steam enhanced catalytically cracked product stream including olefins, benzene, toluene, xylene, naphtha, or combinations thereof; and steam enhanced catalytically cracking the heavy $C_{5+}$ hydrocarbon stream to form a heavy steam enhanced catalytically cracked product stream including olefins, benzene, toluene, xylene, naphtha, or combinations thereof, and wherein, a ratio of gas hourly space velocity of steam to gas hourly space velocity of $C_{5+}$ hydrocarbon stream in the first and second steam enhanced catalytic crackers is from 0.1 to 1.1 times steam to $C_{5+}$ hydrocarbon stream.

A second aspect may include the first aspect, and may further include passing at least a portion of the light steam enhanced catalytically cracked stream, the heavy steam enhanced catalytically cracked stream, or both to a final product separator to produce one or more product streams and one or more recycle streams.

A third aspect may include either the first or second aspects, wherein the one or more product streams include a first product stream including ethylene, propylene, butylene, or combinations thereof; and a second product stream including benzene, toluene, xylenes, or combinations thereof.

A fourth aspect may include any one of the first through third aspects, wherein the light $C_{5+}$ hydrocarbon fraction includes $C_{5+}$ hydrocarbons having a $T_{95}$ boiling point of less than 200° C.; and the heavy $C_{5+}$ hydrocarbon fraction includes $C_{5+}$ hydrocarbons having a $T_5$ boiling point of greater than or equal to 200° C.

A fifth aspect may include any one of the second through fourth aspects, wherein hydrotreating the delayed coker product stream and the deasphalted oil stream additionally forms a $C_1$ hydrocarbon stream and a $C_2$-$C_4$ hydrocarbon stream; and the $C_1$ hydrocarbon stream, the $C_2$-$C_4$ hydrocarbon stream, the light $C_{5+}$ hydrocarbon stream, and the heavy $C_{5+}$ hydrocarbon stream together include a hydrotreated product stream.

A sixth aspect may include the fifth aspect, further including methane cracking the $C_1$ hydrocarbon stream to form hydrogen; steam cracking the $C_2$-$C_4$ hydrocarbon stream to form a steam cracked product stream including light olefins, naphtha, and BTX; and passing the steam cracked product stream to the final separator to produce the one or more product streams and the one or more recycle streams.

A seventh aspect may include the sixth aspect, wherein the one or more recycle streams include a methane recycle stream, a steam cracker recycle stream, a hydrotreater recycle stream, a delayed coker recycle stream, or combinations thereof; the steam cracker recycle stream includes $C_2$-$C_4$ hydrocarbons; the hydrotreater recycle stream includes cracked naphtha and light cycle oil having boiling points of between 185° C. to 426° C.; and the delayed coker recycle stream includes heavy cycle oil having boiling points of between 426° C. to 650° C.

A eighth aspect may include the seventh aspect, further including delayed coking the delayed coker recycle stream to form additional delayed coker product stream; hydrotreating the hydrotreater recycle stream to form additional $C_1$ hydrocarbon stream, $C_2$-$C_4$ hydrocarbon stream, light $C_{5+}$ hydrocarbon stream, heavy $C_{5+}$ hydrocarbon stream, or combinations thereof; methane cracking the methane recycle stream to form additional hydrogen; steam cracking the steam cracker recycle stream to form additional steam cracked product stream; and passing the hydrogen to the hydrotreater to be recycled in the hydrotreater.

A ninth aspect may include the eighth aspect, further including steam cracking a $C_2$ portion of the $C_2$-$C_4$ hydrocarbon stream, a $C_2$ portion of the steam cracker recycle stream, or both, to form the steam cracked product stream; and dehydrogenating a $C_3$-$C_4$ portion of the $C_2$-$C_4$ hydrocarbon stream, a $C_3$-$C_4$ portion of the steam cracker recycle stream, or both to form propylene and butylene; and passing the propylene and butylene to the final separator to produce the one or more product streams.

A tenth aspect may include the ninth aspect, further including passing the hydrotreated product stream to a first product separator to separate the $C_1$ hydrocarbon stream, the $C_2$-$C_4$ hydrocarbon stream, the light $C_{5+}$ hydrocarbon stream, and the heavy $C_{5+}$ hydrocarbon stream.

An eleventh aspect may include any one of the first through tenth aspects, further including initially passing the hydrocarbon oil stream through a feed separator to separate the hydrocarbon oil stream into a heavy hydrocarbon fraction and a light hydrocarbon fraction; solvent deasphalting the heavy hydrocarbon fraction to form at least the deasphalted oil stream and the heavy residual hydrocarbons; and steam enhanced catalytically cracking at least the light hydrocarbon fraction in the first steam enhanced catalytic cracker to form the light steam enhanced catalytically cracked product.

A twelfth aspect may include any one of the first through eleventh aspects, wherein the hydrocarbon oil stream includes whole crude oil or crude oil fractions.

A thirteenth aspect may include any one of the sixth through twelfth aspects, wherein the solvent deasphalting unit is operated at a temperature of from 60° C. to 90° C. and a pressure of from 0.1 MPa to 0.4 MPa; the delayed coker is operated at a temperature of from 450° C. to 600° C. and a pressure of from 0.1 MPa to 0.4 MPa; the hydrotreating zone is operated at a temperature of from 370° C. to 500° C. and a pressure of from 0.1 MPa to 0.2 MPa; the steam enhanced catalytic cracking system is operated at a temperature of from 525° C. to 750° C. and a pressure of from 0.1 MPa to 0.2 MPa; the methane cracking zone is operated at a temperature of from 850° C. to 1200° C. and a pressure of from 0.1 MPa to 0.2 MPa; the dehydrogenation unit is operated at a temperature of from 300° C. to 800° C. and a pressure of from 0.001 MPa to 1 MPa; and the steam cracking zone is operated at a temperature of from 800° C. to 950° C. and a pressure of from 0.1 MPa to 0.2 MPa.

The fourteenth aspect may include any one of the first through thirteenth aspects, wherein the deasphalted oil stream includes $C_1$ to $C_{5+}$ hydrocarbons; the heavy residual hydrocarbons include hydrocarbons $C_{5+}$ hydrocarbons having boiling points of between 426° C. to 650° C.; the delayed coker oil stream includes $C_1$ to $C_{5+}$ hydrocarbons having boiling points of less than 650° C.; and the petroleum coke includes hydrocarbons having boiling points of greater than 650° C.

The fifteenth aspect may include any one of the first through fourteenth aspects, and may include an integrated system for the conversion of hydrocarbon oil feed stocks utilizing a delayed coker and steam enhanced catalytic cracker, including a solvent deasphalting unit configured to separate a hydrocarbon oil stream into at least a deasphalted oil stream and heavy residual hydrocarbons, the heavy residual hydrocarbons including at least asphaltenes; the delayed coker fluidly connected to the solvent deasphalting unit and configured to de-coke the heavy residual hydrocarbons into at least a petroleum coke and a delayed coker product stream; a hydrotreater fluidly connected to the solvent deasphalting unit and the delayed coker and configured to hydrotreat at least the deasphalted oil stream and the delayed coker product stream to form a light $C_{5+}$ hydrocarbon stream and a heavy $C_{5+}$ hydrocarbon stream; a first steam enhanced catalytic cracker fluidly connected to the hydrotreater and configured to crack at least a portion of the light $C_{5+}$ hydrocarbon fraction to form a light steam enhanced catalytically cracked product; and a second steam enhanced catalytic cracker fluidly connected to the hydrotreater, in parallel with the first steam enhanced catalytic cracker, and configured to crack at least a portion of the heavy $C_{5+}$ hydrocarbon fraction to form a heavy steam enhanced catalytically cracked product, and wherein a ratio of gas hourly space velocity of steam to gas hourly space velocity of $C_{5+}$ hydrocarbon stream in the first and second steam enhanced catalytic crackers is from 0.1 to 1.1 times steam to $C_{5+}$ hydrocarbon stream.

A sixteenth aspect may include the fifteenth aspect, further including a final product separator fluidly connected to the first and second steam enhanced catalytic crackers and configured to separate at least a portion of the light and heavy steam enhanced catalytically cracked products into at least one or more product streams and one or more recycle streams, and wherein, the one or more recycle streams include a methane recycle stream, a steam cracker recycle stream, a hydrotreater recycle stream, and a delayed coker recycle stream; the steam cracker recycle stream includes $C_2$-$C_4$ hydrocarbons; the hydrotreater recycle stream includes cracked naphtha, light cycle oil, or both; and the delayed coker recycle stream includes heavy cycle oil.

A seventeenth aspect may include the sixteenth aspect, further including a methane cracker fluidly connected to the hydrotreater and final product separator and configured to crack a $C_1$ hydrocarbon stream, the methane recycle stream, or both, to form hydrogen for recycling in the hydrotreater; and a steam cracker fluidly connected to the hydrotreater and final product separator and configured to crack a $C_2$-$C_4$ hydrocarbon stream, the steam cracker recycle stream, or both, to form a steam cracked product stream including light olefins, naphtha, and BTX for separation in the final product separator; and wherein, the hydrotreater is additionally configured to form the $C_1$ hydrocarbon stream and the $C_2$-$C_4$ hydrocarbon stream; the hydrotreater is fluidly connected to the final product separator and additionally configured to hydrotreat the hydrotreater recycle stream to produce additional $C_1$ hydrocarbon stream, $C_2$-$C_4$ hydrocarbon stream, light $C_{5+}$ hydrocarbon stream, heavy $C_{5+}$ hydrocarbon stream, or combinations thereof; the delayed coker is fluidly connected to the final product separator and additionally configured to de-coke the delayed coker recycle stream to form additional petroleum coke and delayed coker product stream; and the final product separator is configured to send the methane recycle stream to the methane cracker, the steam cracker recycle stream to the steam cracker, the hydrotreater recycle stream to the hydrotreater, and the delayed coker recycle stream to the delayed coker.

An eighteenth aspect may include the seventeenth aspect, further including a dehydrogenation unit fluidly connected to the hydrotreater and the final product separator and configured to dehydrogenate a $C_3$-$C_4$ portion of the $C_2$-$C_4$ hydrocarbon stream, a $C_3$-$C_4$ portion of the steam cracker recycle stream, or both to form propylene and butylene, and wherein, the steam cracker is configured to crack a $C_2$ portion of the $C_2$-$C_4$ hydrocarbon stream, a $C_2$ portion of the steam cracker recycle stream, or both to form light olefins, naphtha, and BTX; and the dehydrogenation unit is additionally configured to send the propylene and butylene to the final product separator.

The nineteenth aspect may include the eighteenth aspect, further including a first product separator fluidly connected to the hydrotreater, the methane cracker, the steam cracker, the first steam enhanced catalytic cracker, and the second steam enhanced catalytic cracker, and wherein the first product separator is configured to separate the hydrotreated product stream into the $C_1$ hydrocarbon stream for the methane cracker; the first product separator is also configured to separate the hydrotreated product stream into the $C_2$-$C_4$ hydrocarbon stream for the steam cracker; the first product separator is also configured to separate the hydrotreated product stream into the light $C_{5+}$ hydrocarbon stream for the first steam enhanced catalytic cracker; and the first product separator is also configured to separate the hydrotreated product stream into the heavy $C_{5+}$ hydrocarbon stream for the second steam enhanced catalytic cracker.

A twentieth aspect may include any one of the fifteenth through nineteenth aspects, further including a feed separator fluidly connected to the solvent deasphalting unit and the first steam enhanced catalytic cracker and configured to separate the hydrocarbon oil stream into a light oil fraction stream and a heavy oil fraction stream, and wherein, the solvent desasphalting unit is configured to separate the heavy oil fraction into at least the heavy residual hydrocarbons and the de-asphalted oil stream; and the first steam enhanced catalytic cracker is configured to crack the light oil fraction stream into the light steam enhanced catalytically cracked product.

A twenty-first aspect may include any one of the fifteenth through twentieth aspects, wherein the first steam enhanced catalytic cracker is additionally configured to form a olefin to naphtha ratio of from 2:1 to 7:1 olefins to naphtha; and the second steam enhanced catalytic cracker is additionally configured to form a olefin to naphtha ratio of from 1.5:1 to 0.8:1 olefins to naphtha.

A twenty-second aspect may include any one of the first through fourteenth aspect, wherein steam enhanced catalytically cracking the light $C_{5+}$ hydrocarbon stream forms the olefins and the naphtha in a ratio of from 2:1 to 7:1 olefins to naphtha; and steam enhanced catalytically cracking the heavy $C_{5+}$ hydrocarbon stream forms the olefins and the naphtha in a ratio of from 1.5:1 to 0.8:1 olefins to naphtha.

It is noted that recitations in the present disclosure of a component of the present disclosure being "operable" or "sufficient" in a particular way, to embody a particular property, or to function in a particular manner, are structural recitations, as opposed to recitations of intended use. More specifically, the references in the present disclosure to the manner in which a component is "operable" or "sufficient" denotes an existing physical condition of the component and, as such, is to be taken as a definite recitation of the structural characteristics of the component.

It is also noted that terms like "preferably," "commonly," and "typically," when utilized herein, are not utilized to limit the scope of the claimed invention or to imply that certain features are critical, essential, or even important to the structure or function of the claimed invention. Rather, these terms are merely intended to identify particular aspects of an embodiment of the present disclosure or to emphasize alternative or additional features that may or may not be utilized in a particular embodiment of the present disclosure.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

Having described the subject matter of the present disclosure in detail and by reference to specific embodiments, it is noted that the various details disclosed in the present disclosure should not be taken to imply that these details relate to elements that are essential components of the various embodiments described in the present disclosure. Further, it will be apparent that modifications and variations are possible without departing from the scope of the present disclosure, including, but not limited to, embodiments defined in the appended claims.

The singular forms "a", "an" and "the" include plural referents, unless the context clearly dictates otherwise.

Throughout this disclosure ranges are provided. It is envisioned that each discrete value encompassed by the ranges are also included. Additionally, the ranges which may be formed by each discrete value encompassed by the explicitly disclosed ranges are equally envisioned.

As used herein and in the appended claims, the words "comprise," "has," and "include" and all grammatical variations thereof are each intended to have an open, non-limiting meaning that does not exclude additional elements or steps.

As used herein, terms such as "first" and "second" are arbitrarily assigned and are merely intended to differentiate between two or more instances or components. It is to be understood that the words "first" and "second" serve no other purpose and are not part of the name or description of the component, nor do they necessarily define a relative location, position, or order of the component. Furthermore, it is to be understood that the mere use of the term "first" and "second" does not require that there be any "third" component, although that possibility is contemplated under the scope of the present disclosure.

What is claimed is:

1. An integrated process for upgrading a hydrocarbon oil feed stream utilizing a delayed coker, steam enhanced catalytic cracker and a dehydrogenation unit, the method comprising:
    solvent deasphalting the hydrocarbon oil stream to form at least a deasphalted oil stream and heavy residual hydrocarbons, the heavy residual hydrocarbons comprising at least asphaltenes;
    delayed coking the heavy residual hydrocarbons to form petroleum coke and a delayed coker product stream;
    hydrotreating the delayed coker product stream and the deasphalted oil stream to form a $C_3$-$C_4$ hydrocarbon stream, a light $C_{5+}$ hydrocarbon stream, and a heavy $C_{5+}$ hydrocarbon stream;
    dehydrogenating the $C_3$-$C_4$ hydrocarbon stream to form propylene and butylene;
    steam enhanced catalytically cracking the light $C_{5+}$ hydrocarbon stream in a first steam enhanced catalytic cracker to form a light steam enhanced catalytically cracked product comprising olefins, benzene, toluene, xylene, naphtha, or combinations thereof; and
    steam enhanced catalytically cracking the heavy $C_{5+}$ hydrocarbon stream in a second steam enhanced catalytic cracker to form a heavy steam enhanced catalytically cracked product comprising olefins, benzene, toluene, xylene, naphtha, or combinations thereof, and wherein,
a first ratio of gas hourly space velocity of steam to gas hourly space velocity of the light $C_{5+}$ hydrocarbon stream in the first steam enhanced catalytic cracker is less than a second ratio of gas hourly space velocity of steam to gas hourly space velocity of the heavy $C_{5+}$ hydrocarbon stream in the second steam enhanced catalytic cracker,
the first ratio is from 0.2 to 0.8, and
the second ratio is from 0.8 to 1.0.

2. The process of claim 1, further comprising passing at least a portion of the propylene, the butylene, the light steam enhanced catalytically cracked product, the heavy steam enhanced catalytically cracked product, or combinations thereof to a final product separator to produce one or more product streams and one or more recycle streams.

3. The process of claim 1, wherein the one or more product streams comprise:
a first product stream comprising ethylene, propylene, butylene, or combinations thereof; and
a second product stream comprising benzene, toluene, xylenes, or combinations thereof.

4. The process of claim 1, wherein:
the light $C_{5+}$ hydrocarbon fraction comprises $C_{5+}$ hydrocarbons having a $T_{95}$ boiling point of less than 200° C.; and
the heavy $C_{5+}$ hydrocarbon fraction comprises $C_{5+}$ hydrocarbons having a $T_5$ boiling point of greater than or equal to 200° C.

5. The process of claim 2, wherein
hydrotreating the delayed coker product stream and the deasphalted oil stream additionally forms a $C_1$ hydrocarbon stream and a $C_2$ hydrocarbon stream; and
the $C_1$ hydrocarbon stream, the $C_2$ hydrocarbon stream, the $C_3$-$C_4$ hydrocarbon stream, the light $C_{5+}$ hydrocarbon stream, and the heavy $C_{5+}$ hydrocarbon stream together comprise a hydrotreated product stream.

6. The process of claim 5, further comprising:
methane cracking the $C_1$ hydrocarbon stream to form hydrogen;
steam cracking the $C_2$ hydrocarbon stream to form a steam cracked product stream comprising light olefins, naphtha, and BTX;
passing the steam cracked product stream to the final separator to thereby separate the olefins, the naphtha, and the BTX, and to thereby produce the one or more product streams and the one or more recycle streams, wherein the one or more recycle streams comprise a methane recycle stream, a steam cracker recycle stream, a hydrotreater recycle stream, and a delayed coker recycle stream;
delayed coking the delayed coker recycle stream to form additional delayed coker product stream, wherein the delayed coker recycle stream comprises heavy cycle oil having boiling points of between 426° C. to 650° C.;
hydrotreating the hydrotreater recycle stream to form additional $C_1$ hydrocarbon stream, $C_2$-$C_4$ hydrocarbon stream, light $C_{5+}$ hydrocarbon stream, heavy $C_{5+}$ hydrocarbon stream, or combinations thereof, wherein the hydrotreater recycle stream comprises cracked naphtha and light cycle oil having boiling points of between 185° C. to 426° C.;
methane cracking the methane recycle stream to form additional hydrogen;
steam cracking the steam cracker recycle stream to form additional steam cracked product stream, wherein the steam cracker recycle stream comprises $C_2$-$C_4$ hydrocarbons; and
passing the hydrogen to the hydrotreater to be recycled in the hydrotreater.

7. The process of claim 6, further comprising passing the hydrotreated product stream to a first product separator to separate the $C_1$ hydrocarbon stream, the $C_2$-$C_4$ hydrocarbon stream, the light $C_{5+}$ hydrocarbon stream, and the heavy $C_{5+}$ hydrocarbon stream.

8. The process of claim 1, further comprising
initially passing the hydrocarbon oil stream through a feed separator to separate the hydrocarbon oil stream into a heavy hydrocarbon fraction and a light hydrocarbon fraction;
solvent deasphalting the heavy hydrocarbon fraction to form at least the deasphalted oil stream and the heavy residual hydrocarbons; and
steam enhanced catalytically cracking at least the light hydrocarbon fraction in the first steam enhanced catalytic cracker to form the light steam enhanced catalytically cracked product.

9. The process of claim 1, wherein the hydrocarbon oil stream comprises whole crude oil or crude oil fractions.

10. The process of claim 6, wherein:
the solvent deasphalting unit is operated at a temperature of from 60° C. to 90° C. and a pressure of from 0.1 MPa to 0.4 MPa;
the delayed coker is operated at a temperature of from 450° C. to 600° C. and a pressure of from 0.1 MPa to 0.4 MPa;
the hydrotreating zone is operated at a temperature of from 370° C. to 500° C. and a pressure of from 0.1 MPa to 0.2 MPa;
the steam enhanced catalytic cracking system is operated at a temperature of from 525° C. to 750° C. and a pressure of from 0.1 MPa to 0.2 MPa;
the methane cracking zone is operated at a temperature of from 850° C. to 1200° C. and a pressure of from 0.1 MPa to 0.2 MPa;
the dehydrogenation unit is operated at a temperature of from 300° C. to 800° C. and a pressure of from 0.001 MPa to 1 MPa; and
the steam cracking zone is operated at a temperature of from 800° C. to 950° C. and a pressure of from 0.1 MPa to 0.2 MPa.

11. The process of claim 1, wherein:
the deasphalted oil stream comprises $C_1$ to $C_{5+}$ hydrocarbons;
the heavy residual hydrocarbons comprise hydrocarbons $C_{5+}$ hydrocarbons having boiling points of between 426° C. to 650° C.;
the delayed coker oil stream comprises $C_1$ to $C_{5+}$ hydrocarbons having boiling points of less than 650° C.; and
the petroleum coke comprises hydrocarbons having boiling points of greater than 650° C.

12. The process of claim 1, wherein:
steam enhanced catalytically cracking the light $C_{5+}$ hydrocarbon stream in the first steam enhanced catalytic cracker forms the olefins and the naphtha in a ratio of from 2:1 to 7:1 olefins to naphtha; and
steam enhanced catalytically cracking the heavy $C_{5+}$ hydrocarbon stream in the second steam enhanced catalytic cracker forms the olefins and the naphtha in a ratio of from 1.5:1 to 0.8:1 olefins to naphtha.

13. The process of claim 12, wherein:
the first steam enhanced catalytic cracker operates with a residence time of from 3 seconds to 10 seconds, a hourly space velocity of from 0.1 $h^{-1}$ to 1 $h^{-1}$, or both; and
the second steam enhanced catalytic cracker operates with a residence time of from 1 second to 3 seconds, a hourly space velocity of from 9 $h^{-1}$ to 40 $h^{-1}$, or both.

* * * * *